United States Patent
Fukui

(10) Patent No.: US 7,336,997 B2
(45) Date of Patent: Feb. 26, 2008

(54) HEART TREATMENT EQUIPMENT AND HEART TREATMENT METHOD

(75) Inventor: Yoshihito Fukui, Kanagawa (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 73 days.

(21) Appl. No.: 11/233,109

(22) Filed: Sep. 23, 2005

(65) Prior Publication Data

US 2006/0052831 A1  Mar. 9, 2006

Related U.S. Application Data

(63) Continuation of application No. PCT/JP2004/003766, filed on Mar. 19, 2004.

(30) Foreign Application Priority Data

Mar. 24, 2003  (JP) ............................ P2003-081017

(51) Int. Cl.
*A61N 1/365* (2006.01)

(52) U.S. Cl. .............................. 607/17; 607/9; 607/14; 607/18; 607/19; 607/20; 607/25; 607/28; 600/509; 600/515

(58) Field of Classification Search .................... 607/9, 607/14, 15, 28, 17–20, 25; 600/509, 518
See application file for complete search history.

(56) References Cited

U.S. PATENT DOCUMENTS

| | | | |
|---|---|---|---|
| 4,719,921 A | | 1/1988 | Chirife |
| 5,658,318 A | * | 8/1997 | Stroetmann et al. ........... 607/6 |
| 6,266,555 B1 | * | 7/2001 | Werner et al. ............... 600/523 |
| 6,473,644 B1 | | 10/2002 | Terry, Jr. et al. |
| 6,873,870 B2 | * | 3/2005 | Ferek-Petric ................. 600/518 |
| 2003/0040774 A1 | * | 2/2003 | Terry et al. ..................... 607/2 |

FOREIGN PATENT DOCUMENTS

| | | |
|---|---|---|
| EP | 0 219 943 A2 | 4/1987 |
| EP | 0 688 577 A1 | 12/1995 |
| EP | 0 688 578 A1 | 12/1995 |
| JP | 62-137068 | 6/1987 |
| JP | 8-38626 | 2/1996 |
| JP | 8-52121 | 2/1996 |
| JP | 11-319119 | 11/1999 |
| JP | 2003-511163 | 3/2003 |
| WO | 01/26729 A1 | 4/2001 |

* cited by examiner

*Primary Examiner*—Kennedy J. Schaetzle
*Assistant Examiner*—Natasha Patel
(74) *Attorney, Agent, or Firm*—Buchanan Ingersoll & Rooney PC

(57) ABSTRACT

Heart treatment equipment and a heart treatment method directed to prevention of a fatal arrhythmia by detecting a physical exercise or a mental stress by using a sensor and thereafter controlling the vagus nerve stimulation, wherein sensor means for detecting various living body information for generating a signal which designates degree of a sympathetic tone is provided and heart rate threshold for carrying out the vagus nerve stimulation is adjusted according to the living body information detected by the sensor means. Further, a nerve stimulation parameter for adjusting the strength of the vagus nerve stimulation is adjusted in response to the degree of the patient sympathetic tone.

33 Claims, 18 Drawing Sheets

FIG. 15

Relation Between QT Time And Heart Rate Threshold

| QT Time | Heart Rate Threshold (Time/Min) |
|---|---|
| ~0.9 × QTnormal | 100 |
| 0.9 × QTnormal | 90 |
| 0.8 × QTnormal | 80 |
| 0.7 × QTnormal | 75 |
| 0.6 × QTnormal | 70 |

QTnormal=~400msec

HEART TREATMENT EQUIPMENT AND HEART TREATMENT METHOD

This application is a continuation of International Application No. PCT/JP2004/003766, having an international filing date of Mar. 19, 2004 and designating the United States.

1. Technical Field

The present invention relates to heart treatment equipment and a heart treatment method which prevent a fatal arrhythmia by an electric stimulation of a vagus nerve and more particularly to heart treatment equipment and a heart treatment method in which it makes it possible to control a tolerance range of a heartbeat parameter in response to a physical exercise or a stress.

2. Background Art

FIGS. 20A and 20B show a constitutional diagram of a heart and an electrocardiogram waveform of a heart respectively. A heart is constituted by two atriums and two ventricles. The atriums are chambers for storing the returned blood and the ventricles are chambers for ejecting the blood. With respect to the blood, the venous blood enters the right atrium through a large vein and is ejected to a pulmonary artery passing through the right atrium and the right ventricle. The arterial blood which takes in oxygen in lungs goes into a left atrium through the pulmonary vein and is ejected to the aorta passing through the left atrium and the left ventricle. The thickness of the ventricle is thicker than that of the atrium, and additionally, in order to prevent backflow of the blood, valves are provided between the right atrium and the right ventricle, between the right ventricle and the pulmonary artery, between the left atrium and the left ventricle and between the left ventricle and the aorta respectively. The condition where the heart loses its ability to maintain adequate blood circulation in the peripheral tissues and the lungs is a heart failure and in many cases, left heart failure where the pumping ability of the left ventricle is primarily affected is caused.

Though there are individual differences, the beating of the heart counts about 100,000 times in a day. Then, a weak current is emitted every heartbeat, so that it is possible to know the condition of the heart by detecting this current. An electrocardiogram of FIG. 20B shows a time course of the electrical activity of the normal heart. This electrocardiogram is obtained from electrodes placed on the skin in specific locations and is consisting of a plurality of waves which have amplitudes of several millivolts. As shown in the drawing, first, a wave which comes first is a P wave and this represents a current in a case when the atria (the right atrium and left atrium) depolarize. The wave which comes next is a wave called as a QRS wave and this is a wave of ventricular depolarization. The wave which comes next is a T wave and this is a current when the ventricles (the right ventricle and the left ventricle) repolarize.

A PQ time begins at the onset of the P wave and to the onset of the QRS wave and represents the time between the start of atrial depolarization and the start of the ventricular depolarization. A QT time begins at the onset of the QRS wave and to the end of the T wave and represents the time between the start of ventricular depolarization and the end of ventricular repolarization.

A sudden death especially caused by a heart disease is called a sudden cardiac death and the number thereof reaches about annual 50,000 people in Japan. The immediate cause of the sudden cardiac death is the ventricle tachycardia with hemodynamic compromise or the ventricle fibrillation, which are called a fatal arrhythmia.

When the ventricle tachycardia which is abnormal rapid heartbeat or the ventricle fibrillation which is extremely rapid chaotic heartbeat occurs, the pumping function of the heart lowers or disappears and it becomes impossible to fill with enough blood to supply the whole body. For this reason, unconsciousness is caused in accordance with the decrease in the cerebral blood flow, so that a death might be caused unless an immediately appropriate treatment is conducted.

For a patient having a risk of such a sudden cardiac death, an implantable cardioverter defibrillator (ICD) is implanted. When the ICD detects a ventricle tachycardia or a ventricle fibrillation, it delivers an electrical shock to the heart. However, a high-energy shock is required for defibrillation and there is a danger that the cardiac tissue subjected to the shock could be damaged.

The cardiac activity is put under the control of an autonomic nerve system and the autonomic nerve system has a sympathetic nerve system and a parasympathetic nerve system where the parasympathetic nerve system of the heart is a vagus nerve. When the sympathetic tone increases, the cardiac activity (mainly heart rate and contractility) increases and when the vagal tone increases, the cardiac activity (mainly heart rate) decreases. The activities in the sympathetic nerve and the vagus nerve are usually antagonistic each other and the heart is controlled stably so as to maintain appropriate heartbeats about 70 beats/minute at rest. More specifically, the increase in the sympathetic tone has an excitatory effect on the cardiac activity and on the other hand, the increase in the vagal tone has an inhibitory effect on the cardiac activity.

While an increased vagal tone lowers a heart rate, the lowering of the heart rate decreases the generation of a ventricular premature contraction which induces a fatal arrhythmia, and also, the decrease of the oxygen consumption of the heart muscle owing to the lowering of the heart rate prevents or improve an oxygen shortage situation of the heart muscle such that it prevents the occurrence of a myocardial ischemia, a myocardial infarction and a fatal arrhythmia accompanied thereto.

A heart treatment equipment attempting a stabilization of a heart rate by utilizing such a function and by carrying out an electric stimulation of the vagus nerve has been proposed recently (for example, see the patent document 1). This proposal is such as to control the stimulation frequency of the vagus nerve so as to maintain a heart rate of a patient in a tolerance level which is lower than a lower limit of the heart rate of a patient at rest.

Also, in order to avoid the fatal arrhythmia, it is proposed a method and equipment where an electrical stimulation is given to the vagus nerve (see, for example, the patent document 2). In this equipment for medical treating the heart arrhythmia, it is directed to prevent or stop the heart arrhythmia and to maintain an appropriate function of the heart by way of the stimulation to the heart and the stimulation of the vagus nerve. This heart treatment equipment not only compares a pre-set threshold value of a detecting interval of the tachycardia with the beating of the patient, but also carefully examines the ST portion (voltage) change of an intracardiac electrogram which implies an acute myocardial ischemia and other contributing factors relating to the complex tachycardia of the ventricles such that it becomes possible to prevent the tachycardia based on that result. The heart arrhythmia treatment equipment is constituted by means for continuously measuring an intracardiac electrogram of a patient heart, means for detecting a characteristic which shows the tachycardia of the aforesaid intracardiac electrogram, means for initializing memories of a series of characteristics, means for supplying one or more electrical stimulations to a patient nerve system, and means for initializing a series of characteristics of the intracardiac electrogram subsequent to the supply of aforesaid stimulating action.

[Patent Document 1]
US Patent Published Patent Application of U.S. Pat. No. 6,473,644

[Patent Document 2]
Pamphlet of WIPO Laid-open Patent WO 93/21824 (PCT/US93/00051)

DISCLOSURE OF THE INVENTION

The excessive stimulation of the vagus nerve has a problem with having discomfort or uncomfortable feelings caused by suppressing the physiological heart activity, short breath, palpitation and fatigablity caused by suppressing a heart rate increase to be small, and as an influence to organs other than the heart, for example, indigestion and vomiturition owing to an excessive secretion of gastric acid, insulin, glucagons and the like or cough increase, pharyngitis, laryngismus, paresthesia, dyspnea and asthmatic attack for patients with a history of asthma, and if an enough stimulation of the vagus nerve is not performed conversely, there is a problem antagonistically that enough effect cannot be obtained, so that it was demanded to control the vagus nerve stimulation within an allowable range in response to the situation for stabilizing the heart rate.

The equipment described in the patent document 1 is built-in with a simple real-time clock utilizing a clock signal supplied for operating an electronic circuit of the equipment in which the circadian rhythm is realized in a tolerance level of heart rate stabilization according to that clock by changing the tolerance level of the heart rate stabilization by the vagus nerve stimulation to a tolerance level which is made correspondence with a bedtime or an activity time beforehand when it reaches a time set beforehand, for example, a bedtime or an activity time. However, a life pattern is always changing even in an ordinary daily life and it cannot have correspondence at all in a case when an overseas trip is executed in which especially day and night is reversed.

Also, the equipment described in the patent document 2 is directed to prevent a tachycardia or a fibrillation beforehand by detecting an ST value (voltage) from the intracardiac electrogram information and by emitting a trigger for a nerve stimulation whether or not the value goes over the threshold and at the same time, the heart is stimulated in order to overcome the decrease of the heart rate owing to the vagus nerve stimulation making the heart rate be in a tolerance range, but the allowable range of the heart rate could not be controlled in response to the situation. Also, the ST value is a value showing an ischemia state of a heart muscle or an injury degree of a heart muscle and further, it changes at an acute stage of the ischemia but returns to a normal level at a chronic stage, so that it was difficult for the nerve stimulation control according to the ST value to realize the prevention under the various situations experienced daily.

Patients with organic heart disease (myocardial infarction, cardiomyopathy and the like) have a risk of developing a fatal arrhythmia. It is known for this development of a fatal arrhythmia that autonomic tone, especially increase of a sympathetic tone is strongly concerned in. The increase of the sympathetic tone makes arrhythmia easy to develop by increasing of automaticity of the heart muscle or the stimulus conduction system or by shortening a refractory period of excitement. The concernment of the increase of the sympathetic tone is also suggested by a report that there are a lot of sudden deaths in patient with organic heart disease for decreaseing of vagal tone or disappearing circadian rhythm.

Generally, the sympathetic tone is increased by a physical exercise or a mental stress. Especially for an organic heart diseased patient, the risk of developing a fatal arrhythmia is heightened by an organic lesion of the heart and the increase of the sympathetic tone being combined.

Consequently, the present invention has an object to offer heart treatment equipment wherein the degree of the sympathetic tone is detected indirectly by detecting a physical exercise, a mental stress or the like by means of a sensor and in a case when it is judged by the detected physical exercise, mental stress or the like that the sympathetic tone is intense, the upper limit rate of the spontaneous heart rate which carries out the vagus nerve stimulation is made low such that the heart rate is stabilized within a narrower range in order to prevent a fatal arrhythmia and in a case when it is judged by a physical exercise, a mental stress or the like that the sympathetic tone is little and the risk of developing a fatal arrhythmia is few, it is possible to control the upper limit rate of the spontaneous heart rate which activates the vagus nerve stimulation to be high such that the range containing the heart rate becomes wide in order to lower or to avoid having discomfort or uncomfortable feelings of a patient, alternatively, short breath, palpitation or fatigability and furthermore, side-effects as an influence to organs other than the heart.

In order to solve aforesaid problems and to achieve the object of the present invention, the heart treatment equipment of the present invention has a specific feature in which there are provided with nerve stimulation means for generating a nerve stimulation signal which stimulates a vagus nerve; heart activity measuring means for measuring a heart activity; heart activity threshold control means for setting a heart activity threshold when stimulating the vagus nerve by the nerve stimulation means; heart activity comparing means for comparing an output of the heart activity measuring means and the threshold; and sensor means for sensing a living body information, wherein the heart activity threshold control means controls the threshold in response to an output of the sensor means.

Also, the heart treatment equipment of the present invention has a feature in which the heart activity measuring means measures a heart rate and the nerve stimulation means generates the nerve stimulation signal in a case when the measured heart rate exceeds the threshold or the heart treatment equipment of the present invention has a feature in which the heart activity measuring means measures a heartbeat interval and the nerve stimulation means generates the nerve stimulation signal in a case when the measured heartbeat interval goes under the threshold.

Further, the heart treatment equipment of the present invention has a feature in which nerve stimulation signal control means for controlling a parameter of the nerve stimulation signal in response to an output of the sensor means is included and for the parameter of this nerve stimulation signal, at least one of a period between pulses, a pulse width, a number of pulses, a pulse voltage, a pulse current, a delay time, a rest time and a repetitive number or a multiple combination chosen therefrom is used.

Also, the heart treatment equipment of the present invention has a feature in which the sensor means is to sense a ventricle contractility and as for this ventricle contractility, it is related to any one of a QT time, an intraventricular electrogram area, a pre-ejection time, a stroke volume and a ventricle pressure.

Further, the heart treatment equipment of the present invention has a feature in which the sensor means is to sense a body motion, is to sense breathing or is to sense blood.

Also, the heart treatment equipment of the present invention has a feature in which there are provided with nerve stimulation means for generating a nerve stimulation signal which stimulates a vagus nerve; heart activity measuring means for measuring an atrium activity; heart activity threshold control means for setting a heart activity threshold when stimulating the vagus nerve by the nerve stimulation means; means for comparing an output of the heart activity measuring means and threshold; sensor means for sensing a ventricle contractility; atrioventricular delay time measuring means for starting a clocking in response to the atrium activity; and atrioventricular delay time comparator means for emanating an output which carries out a ventricle stimulation when an output of the atrioventricular delay time measuring means exceeds a predetermined set value, wherein the sensor means senses the ventricle contractility concurrently with the ventricle stimulation and the heart activity threshold control means controls the threshold in response to an output of the sensor means.

Further, the heart treatment equipment of the present invention has a feature in which the sensor means sensing the ventricle contractility is an intracardiac electrogram sensor and this intracardiac electrogram sensor is either one of a QT time sensor and an intraventricular electrogram area sensor.

Furthermore, it has a feature in which nerve stimulation signal control means for controlling a parameter of the nerve stimulation signal in response to the output of the sensor means is included and the parameter of this nerve stimulation signal is at least one of a period between pulses, a pulse width, a number of pulses, a pulse voltage, a pulse current, a delay time, a rest time and a repetitive number or a multiple combination chosen from these.

Also, the heart treatment method of the present invention has a feature in which there are provided with a step for sensing a living body information; a heart activity measuring step for measuring a heart activity; a heart activity comparing step for comparing the heart activity measuring result with a threshold; and a step for stimulating a vagus nerve in a case when it is judged by the heart activity comparing step that the heart activity increases, wherein there is included a step for changing the threshold in response to the sensed living body information.

Then, the heart treatment method of the present invention has a feature in which a heart rate is measured as the heart activity and a nerve stimulation signal is generated in a case when the measured heart rate exceeds the threshold or a heartbeat interval is measured as the heart activity and a nerve stimulation signal is generated in a case when the measured heartbeat interval goes under the threshold.

Then, the heart treatment method of the present invention has a feature in which the living body information is information relating to a ventricle contractility and the ventricle contractility is related to any one of a QT time, an intraventricular electrogram area, a pre-ejection time, a stroke volume and a ventricle pressure.

Also, the heart treatment method of the present invention has a feature in which the living body information is information relating to a body motion of a patient or information relating to breathing of a patient or information relating to blood of a patient.

Then, further, it has a feature in which nerve stimulation signal control means for controlling a parameter of the nerve stimulation signal in response to the sensed living body information is included and the parameter of this nerve stimulation signal is at least one of a period between pulses, a pulse width, a number of pulses, a pulse voltage, a pulse current, a delay time, a rest time and a repetitive number or a multiple combination chosen from these.

Also, the heart treatment method of the present invention has a feature in which there are provided with a heart activity measuring step for measuring an atrium activity; a heart activity comparing step for comparing the heart activity measuring result with a threshold; a step for stimulating a vagus nerve in a case when it is judged by the heart activity comparing step that the atrium activity increases; a step for sensing a ventricle contractility; a step for starting a clocking of an atrioventricular delay time in response to the atrium activity; a step for comparing whether or not the clocked atrioventricular delay time exceeds a predetermined set value and carrying out a ventricle stimulation when it exceeds the predetermined set value; a step for measuring the ventricle contractility concurrently with the ventricle stimulation; and a step for changing the threshold in response to the measured ventricle contractility.

Then, the heart treatment method of the present invention has a feature in which the step for sensing the ventricle contractility is carried out by an intracaridic electrogram sensor and as for this intracardiac electrogram sensor, either one of a QT time sensor and an intraventricular electrogram area sensor is used.

Further, the heart treatment method of the present invention has a feature in which a parameter of the nerve stimulation signal is to be controlled in response to an output of the sensor and as for the parameter of this nerve stimulation signal, at least one of a period between pulses, a pulse width, a number of pulses, a pulse voltage, a pulse current, a delay time, a rest time and a repetitive number or a multiple combination chosen therefrom is used.

According to the heart treatment equipment and the heart treatment method of the present invention, it is possible to adjust the heart rate threshold on an occasion when the vagus nerve stimulation is carried out in response to the degree of the patient sympathetic tone, so that it is possible to prevent a fatal arrhythmia occurrence and at the same time it is possible to preserve the physiological heart activity of the patient himself and it is possible to increase the physical exercise tolerable ability of the patient and it is possible to avoid side-effects of the nerve stimulation and a situation in which the heart rate is lowered too much. More specifically, in a case when the degree of the sympathetic tone is high, the upper limit rate of the spontaneous heart rate which carries out the vagus nerve stimulation is made low such that the heart rate is stabilized within a narrower range and in a case when the degree of the sympathetic tone is low and the possibility of a fatal arrhythmia occurrence is few, it is possible to control the upper limit rate of the spontaneous heart rate which activates the vagus nerve stimulation to be high such that the range containing the heart rate becomes wide.

BRIEF DESCRIPTION OF DRAWINGS

FIG. 15 is a diagram designating QT times and heart rate thresholds;

BEST MODE FOR CARRYING OUT THE INVENTION

Figure 1:
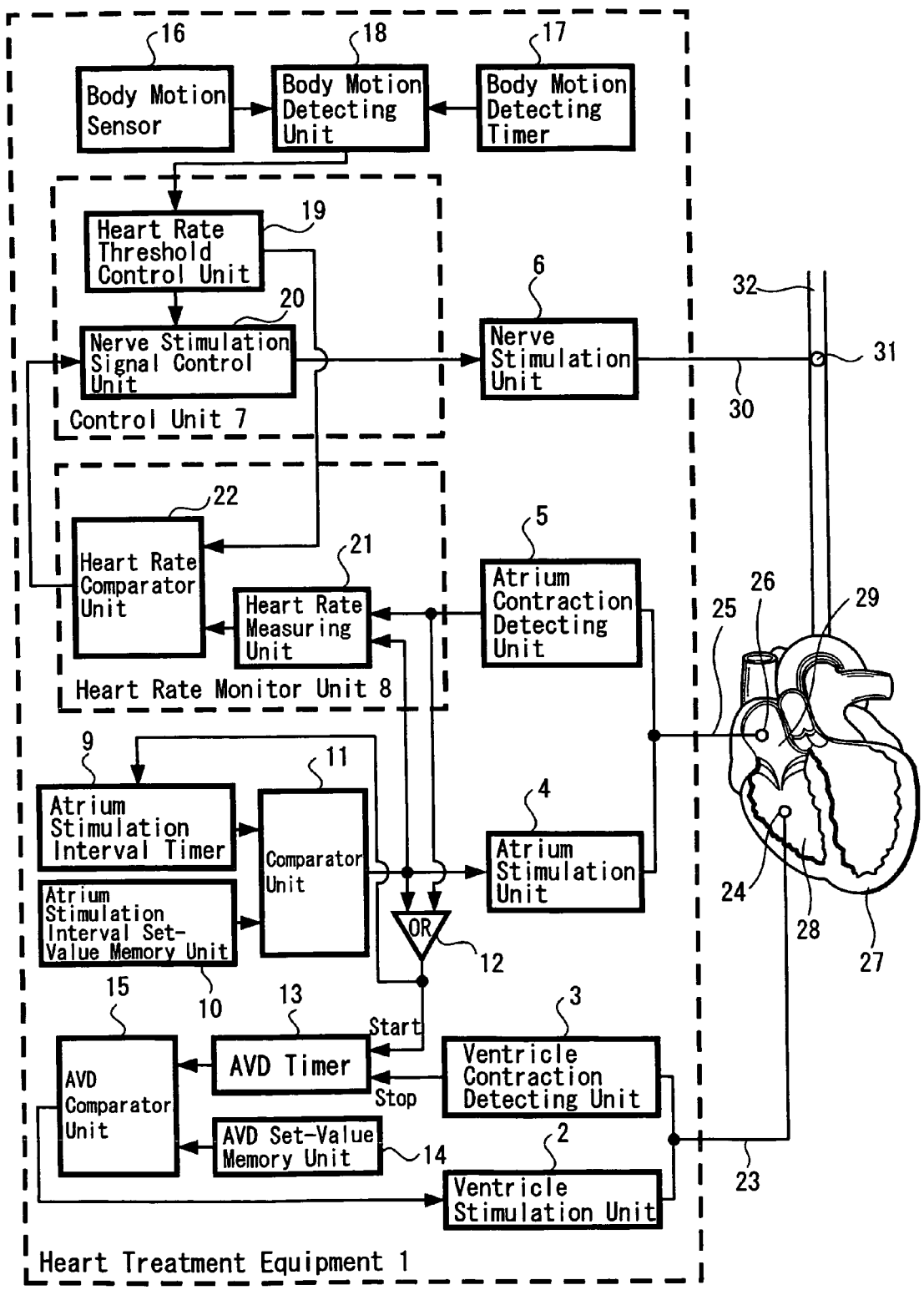
FIG. 1 is a diagram showing a constitutional example of heart treatment equipment of a first exemplified embodiment according to the present invention.

Hereinafter, preferable exemplified embodiments of the present invention will be explained in detail according to attached drawings.

It should be noted that the exemplified embodiments described below are preferable embodiments according to the present invention such that technologically preferable various limitations are added thereto, but the scope of the present invention are not to be limited to these exemplified embodiments so long as there is especially a description in the explanation hereinafter that the present invention is to be limited thereto.

First, a first exemplified embodiment of heart treatment equipment according to the present invention will be described hereinafter in detail with reference to FIG. 1.

Heart treatment equipment 1 of the present invention is constituted by a ventricle stimulation unit 2 for generating a ventricle stimulation pulse stimulating a right ventricle 28 of a heart 27, a ventricle contraction detecting unit 3 for detecting a contraction of the right ventricle 28, an atrium stimulation unit 4 for generating an atrium stimulation pulse stimulating a right atrium 29 of the heart 27, an atrium contraction detecting unit 5 for detecting a contraction of the right atrium 29, a nerve stimulation unit 6 for generating a nerve stimulation signal stimulating a vagus nerve 32, a control unit 7 for controlling the timing of a nerve stimulation signal generation, a heart rate monitor unit 8 for detecting a heart rate by the atrium contraction and for supplying a control signal to the control unit 7, an atrium stimulation interval timer 9 for counting a time interval of the atrium stimulation, an atrium stimulation interval set-value memory unit 10 for storing a threshold interval period for carrying out the atrium stimulation, a comparator unit 11 for emanating an output when the counted value of the atrium stimulation interval timer 9 exceeds the set value stored in the atrium stimulation interval set-value memory unit 10, an OR circuit 12 supplied with outputs of the atrium contraction detecting unit 5 and comparator unit 11, an AVD (atrioventricular delay) timer 13 starting by the output of the OR circuit 12 and being stopped by the output of the ventricle contraction detecting unit 3, an AVD set-value memory unit 14 for storing a normal atrioventricular delay time (AVD), an AVD comparator unit 15 for emanating an output when the counted time of the AVD timer 13 exceeds the set value stored in the AVD set-value memory unit 14 and a body motion sensor 16 for detecting a body motion, a body motion detecting timer 17 for estimating the timing of the body motion detection, and a body motion detecting unit 18 for taking in the output from the body motion sensor 16 at a timing clocked by the body motion detecting timer 17.

Generally, a piezoelectric sensor or an acceleration sensor is used for the body motion sensor 16. The sensor is installed inside a housing of the heart treatment equipment 1 which is implanted in a chest subcutaneously and it is mounted directly on the housing or on a circuit board. In case of the piezoelectric sensor, a stress is added to a piezoelectric crystal by a physical movement and the crystal generates an electrical signal. In case of the acceleration sensor, a structure having a cantilever beam is generally employed and the beam produces movement/displacement by the acceleration so as to generate an electrical signal. It is possible to detect a body motion of a patient by the frequency, the strength or the strength in a certain constant frequency of that electrical signal to be generated.

The control unit 7 is constituted by a heart rate threshold control unit 19 for changing a heart rate threshold in response to the body motion detected in the body motion detecting unit 18 and a nerve stimulation signal control unit 20 for receiving the signal from the heart rate monitor unit 8 and for controlling the nerve stimulation unit 6.

The heart rate monitor unit 8 is constituted by a heart rate measuring unit 21 for measuring the heart rate by the output of the atrium contraction detecting unit 5 and being reset its counting by the output of the atrium contraction detecting unit 5 and the output of the comparator unit 11, that is, the signal triggering the atrium stimulation unit 4 and a heart rate comparator unit 22 for comparing a heart rate which is an output of the heart rate measuring unit 21 and the heart rate threshold stored in the heart rate threshold control unit 19 of the control unit 7.

The ventricle stimulation unit 2 and the ventricle contraction detecting unit 3 are connected to a ventricle stimulation/detection electrode 24 by means of a common ventricle electrode-lead 23 and also the atrium stimulation unit 4 and the atrium contraction detecting unit 5 are similarly connected to an atrium stimulation/detection electrode 26 through an atrium electrode-lead 25. The ventricle stimulation/detection electrode 24 and the atrium stimulation/detection electrode 26 are arranged in the right ventricle 28 and the right atrium 29 of the heart 27 respectively.

Figure 2:
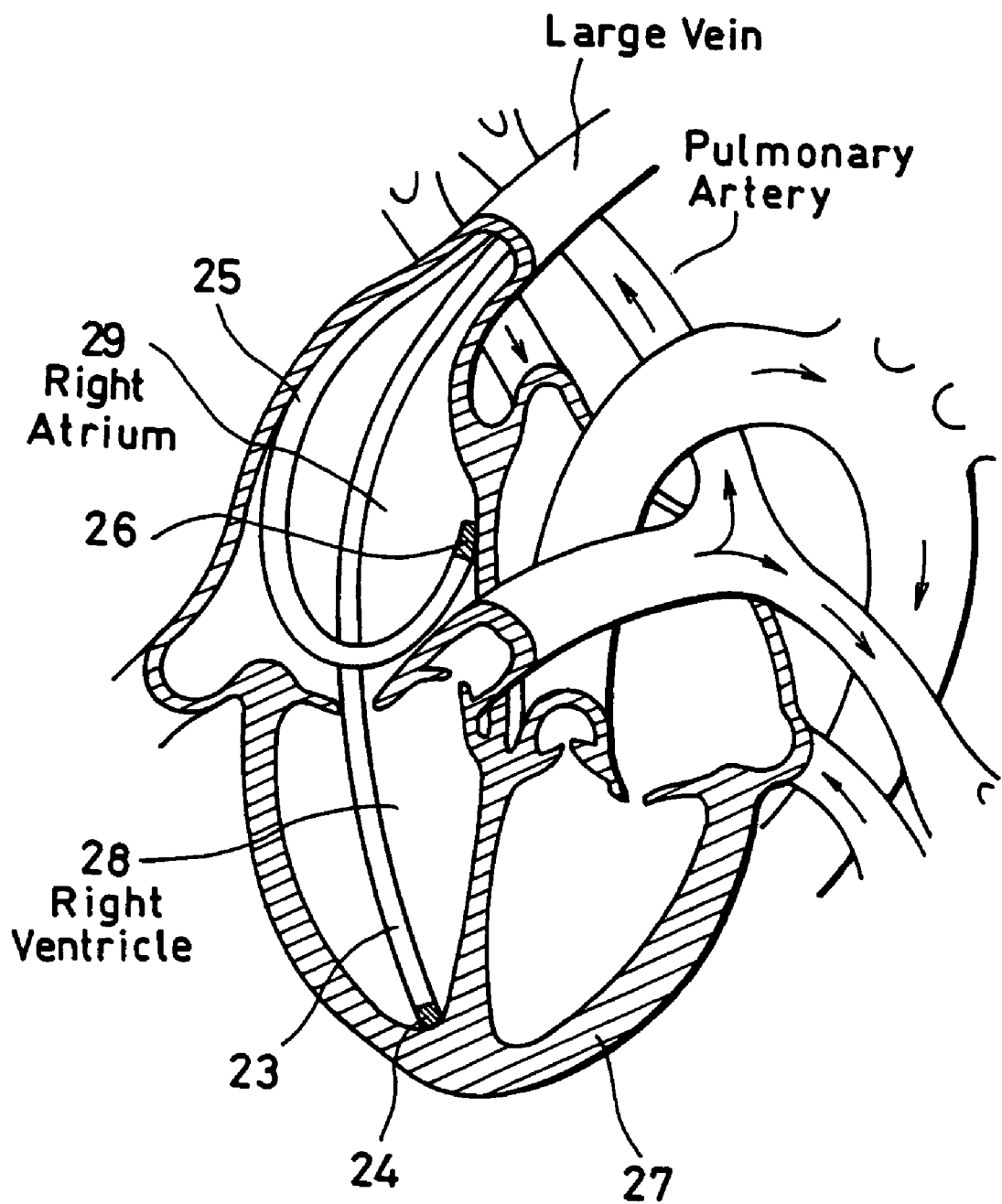
FIG. 2 is a layout diagram of electrode-leads and stimulation/detection electrodes which are used for heart treatment equipment according to the present invention.

Generally, as an electrode for a heart, there is a epicardium electrode embedded in a cardiac muscle and a catheter electrode which is an electrode inserted into the heart through a large vein. FIG. 2 shows an example of catheter electrodes where all of the ventricle electrode-lead 23 and the atrium electrode-lead 25 are introduced to the right atrium 29 of the heart 27 firstly through a large vein. The atrium electrode-lead 25 which is inserted to the right atrium 29 through the large vein is inserted such as being hooked at its bended tip portion of J-shape in a right auricular appendage which protruded from the wall of the right atrium 29 and has a pouched form and the atrium stimulation/detection electrode 26 is arranged such as being contacted with the inner wall of the right auricular appendage. Additionally, the ventricle electrode-lead 23 which is similarly inserted to the right atrium 29 through the large vein enters the right ventricle 28 through an atrioventricular valve and the ventricle stimulation/detection electrode 24 which is provided at the tip portion of the ventricle electrode-lead 23 is arranged such as being contacted with an apex of the right ventricle 28.

Also, the nerve stimulation unit 6 is connected to a nerve stimulation electrode 31 by means of a nerve electrode-lead 30 and the nerve stimulation electrode 31 is fixed to a vagus nerve 32 in a condition of being wrapped thereon. The region where the nerve stimulation electrode 31 is wrapped is preferably selected to be in a cervical region or at a right center position of the external carotid artery. Further, it is also possible to arrange the nerve stimulation electrode 31 so as to stimulate the vagus nerve 32 adjacent to a blood vessel wall by detaining a catheter electrode in the blood vessel. In that case, it is preferable to select the arrangement region in a subclavian vein.

Hereinafter, the operation of a first exemplified embodiment of the heart treatment equipment according to the present invention will be explained.

In FIG. 1, first, when a contraction of the right atrium 29 is detected by the atrium contraction detecting unit 5, the atrium contraction detecting unit 5 transmits its output to a heart rate measuring unit 21 of a heart rate monitor unit 8 and an OR circuit 12. Then, the heart rate measuring unit 21 measures a heart rate from the counted contents including time information when the atrium contraction was detected and it transmits the counted result to the heart rate comparator unit 22. At the same time, the heart rate measuring unit 21 resets its counted result and starts a counting of a time interval until a detection of a next atrium contraction. The heart rate comparator unit 22 emanates an output when the measured value of the heart rate measuring unit 21, that is, the value corresponding to a heart rate per one minute which is calculated by a time interval until the atrium contraction detection exceeds the threshold set in the heart rate threshold control unit 19 of the control unit 7, because it means that the heart activity increases and supplies it to the nerve stimulation signal control unit 20 of the control unit 7. The nerve stimulation signal control unit 20 receives this signal, controls the nerve stimulation unit 6 and stimulates vagus nerve 32.

In addition, the output of the atrium contraction detecting unit 5 is also supplied to the atrium stimulation interval timer 9 by way of the OR circuit 12 and resets the atrium stimulation interval timer 9. The atrium stimulation interval timer 9 is reset according to an output supplied thereto through the OR circuit 12 whenever an atrium spontaneous event or an event by the atrium stimulation occurs and carries out clocking of the atrium event occurrence interval. Then, when this clocked value coincides with the set value stored in the atrium stimulation interval set-value memory unit 10, an output is emanated from the comparator unit 11 and this output is supplied to the atrium stimulation unit 4 and atrium stimulation is carried out. At the same time, the output of the comparator unit 11 is supplied to the atrium stimulation interval timer 9 by way of the OR circuit 12 similarly as an occasion of the atrium contraction detection and resets that. If an atrium spontaneous event is detected in the atrium contraction detecting unit 5 before the counted value of the atrium stimulation interval timer 9 reaches the set value stored in the atrium stimulation interval set-value memory unit 10, the atrium stimulation interval timer 9 is reset at every time and that counted value never reaches the set value stored in the atrium stimulation interval set-value memory unit 10, so that an output is not emanated from the comparator unit 11 and the atrium stimulation is not carried out.

Also, the output of the comparator unit 11 is supplied to the AVD timer 13 by way of the OR circuit 12 together with the output of the atrium contraction detecting unit 5 and makes the counting of the AVD timer 13 start. Further, it is constituted such that the signal which is an output of the comparator unit 11 and triggers atrium stimulation unit 4 is transmitted to the heart rate measuring unit 21 of the heart rate monitor unit 8 and resets the heart rate measuring unit 21. At this time, the heart rate measuring unit 21 only resets that counted result differently with the case of the atrium contraction detection and does not carry out the heart rate measurement and the succeeding output of the counted result. In this manner, it is constituted such that the heart rate measuring unit 21 determines the heart rate corresponding value by the preceding atrium event and the detected time interval of the atrium contraction only when there was a spontaneous atrium contraction and when this heart rate value exceeds the threshold stored in the heart rate threshold control unit 19 of the control unit 7, the heart rate comparator unit 22 generates an output is supplied to the nerve stimulation signal control unit 20 of the control unit 7.

Also, the AVD timer 13 is a timer for measuring a time period after the atrium contraction or stimulation occurs until the ventricle contracts, starts clocking by the atrium contraction or the atrium stimulation and stops its clocking when the ventricle contraction is detected in the ventricle contraction detecting unit 3.

However, in a case when the ventricle contraction detecting unit 3 does not detect contraction of the right ventricle 28 within a predetermined set value stored in the AVD set-value memory unit 14, the clocked value of the AVD timer 13 reaches the set value of the AVD set-value memory unit 14, so that an output is emanated from the AVD comparator unit 15 and transmitted to the ventricle stimulation unit 2. The ventricle stimulation unit 2 receives this signal and carries out the ventricle stimulation by way of the ventricle electrode-lead 23 and the ventricle stimulation electrode 24.

It is constituted when the nerve stimulation signal control unit 20 of the control unit 7 receives the signal from the heart rate comparator unit 22 such that an output thereof is transmitted to the nerve stimulation unit 6 and the nerve stimulation unit 6 carries out stimulation of the vagus nerve 32 through the nerve electrode-lead 30 and the nerve stimulation electrode 31. Here, the body motion sensor 16 can measure the degree of the sympathetic tone by detecting a body acceleration or vibration. This is because a change (acceleration or vibration) of the body motion becomes large when an intense physical exercise is carried out and at the same time, also the sympathetic nerve becomes in a condition of excitement. Then, the output from the body motion sensor 16 is detected by the body motion detecting unit 18 with a proper time interval clocked by the body motion detecting timer 17 and the body motion at each measurement is to be measured. It is possible to change the threshold of the heart rate threshold control unit 19 according to this detected body motion, so that it is possible to change the heart rate threshold for carrying out the nerve stimulation in response to the patient situation.

Figure 3:
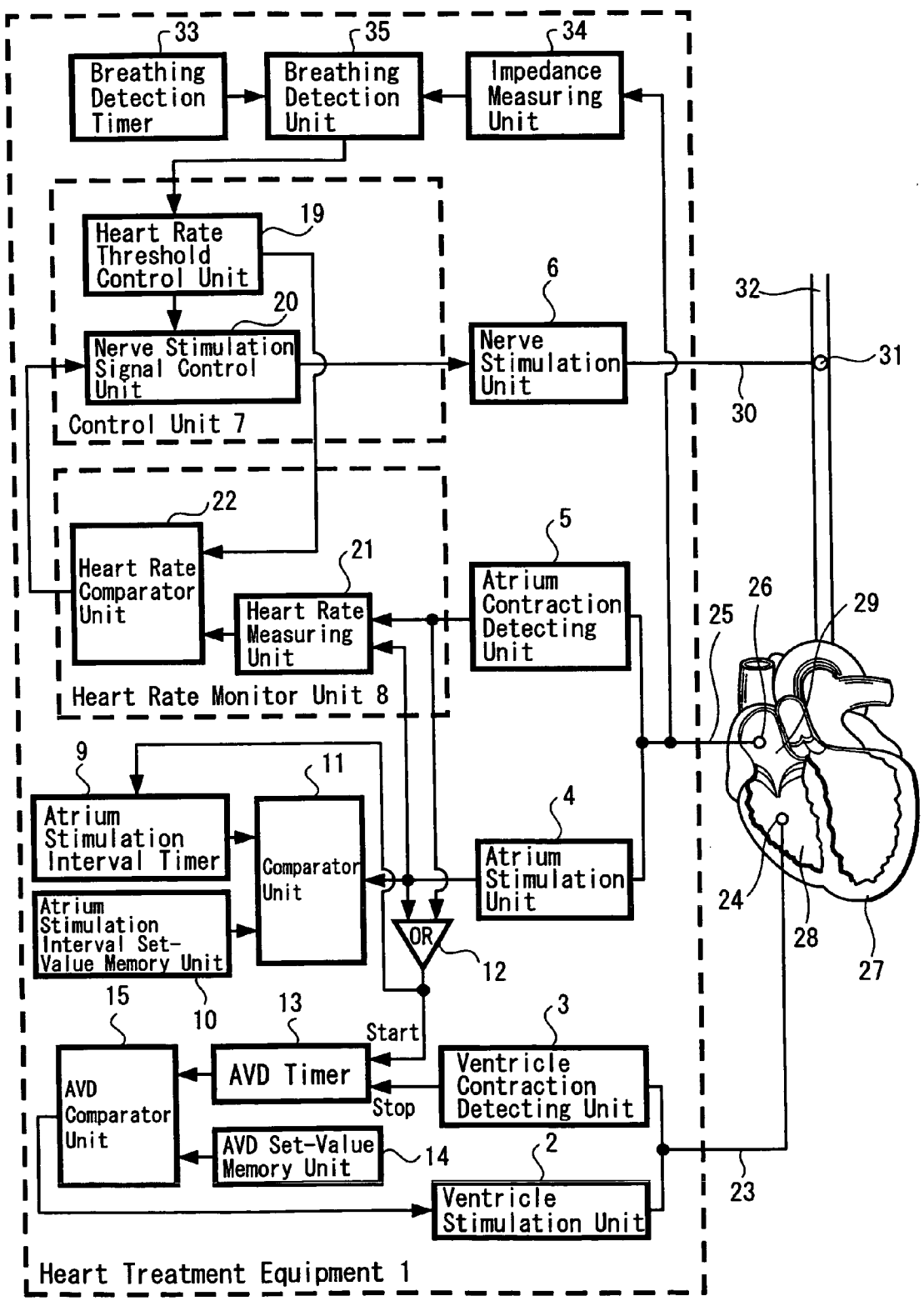
FIG. 3 is a diagram showing a constitutional example of heart treatment equipment of a second exemplified embodiment according to the present invention.

FIG. 3 is a block constitutional diagram showing a second exemplified embodiment of the heart treatment equipment according to the present invention. The portion which is different from the first exemplified embodiment shown in FIG. 1 lies in that a breathing sensor is used as a substitute for the body motion sensor 16. Portions same as those in the block constitutional diagram of FIG. 1 are put with the same reference numerals and the explanation thereof is also omitted.

The breathing sensor is constituted by an impedance measuring unit 34 connected to the atrium electrode-lead 25, a breathing detection unit 35 supplied with an output of the impedance measuring unit 34 and a breathing detection timer 33 for estimating a timing of a breathing detection. The impedance measuring unit 34 superimposes/applies through the atrium electrode-lead 25 a constant current measuring waveform of the strength by which the right atrium 29 is not stimulated to between a titanium housing of the heart treatment equipment 1 implanted in a chest spontaneously and the atrium stimulation/detection electrode 26 and measures an impedance by measuring the voltage of the both ends. In this manner, the breathing sensor can detect an expansion or a contraction of a thorax by an impedance change between the right atrium 29 and the chest region, so that it is possible to detect a breathing state of a patient. It should be noted that the breathing sensor may be constituted such that the impedance measuring unit 34 and the ventricle electrode-lead 23 are connected so as to detect a breathing state of a patient by an impedance change between the right ventricle 28 and the chest region.

Hereinafter, the operation of aforesaid second exemplified embodiment of the heart treatment equipment according to the present invention will be explained. When the degree of the sympathetic tone is heightened by a physical exercise or a stress, the breathing (breathing rate or breathing amount) becomes intense and that is detected as an impedance change in the impedance measuring unit 34 of the breathing sensor through the atrium electrode-lead 25. The breathing detection unit 35 processes the impedance change measured by the impedance measuring unit 34 every proper time which is counted in the breathing detection timer 33, and a breathing rate is detected from the impedance changing speed and a breathing amount is detected from the impedance changing magnitude such that a heart rate threshold of the heart rate threshold control unit 19 is to be changed in response to this breathing rate or this breathing amount. Then, this selected heart rate threshold is supplied to the heart rate comparator unit 22 and is compared with the heart rate measured in the heart rate measuring unit 21.

As the result of this comparison, in a case when the heart rate measured by the heart rate measuring unit 21 exceeds the heart rate threshold, an output can be obtained from the heart rate comparator unit 22, is applied to the nerve stimulation unit 6 by way of the nerve stimulation signal control unit 20 and the stimulation of the vagus nerve 32 is carried out.

Figure 4:
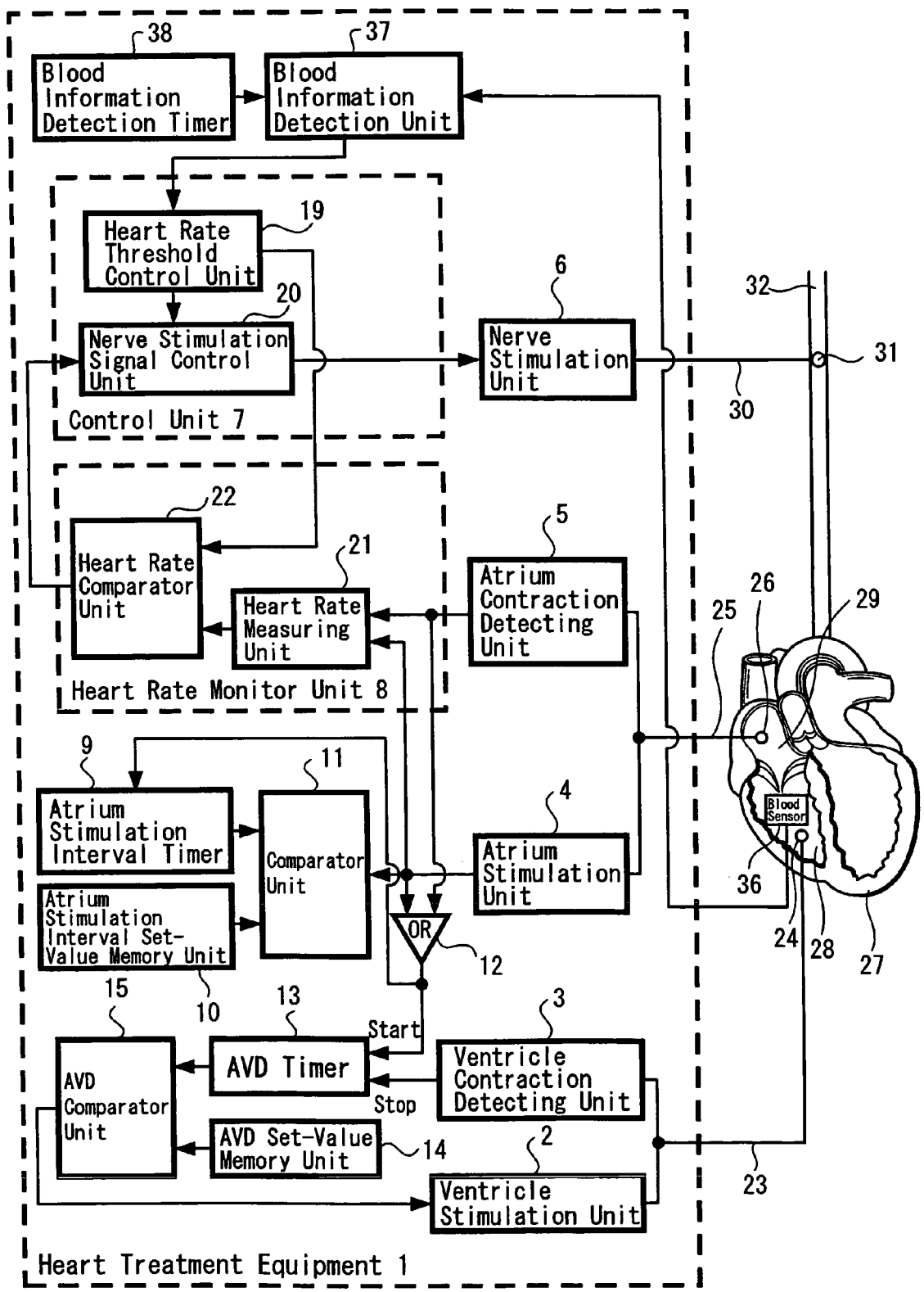
FIG. 4 is a diagram showing a constitutional example of heart treatment equipment of a third exemplified embodiment according to the present invention.

FIG. 4 is a block constitutional diagram showing a third exemplified embodiment of the heart treatment equipment according to the present invention. The portion which is different from the first exemplified embodiment and the second exemplified embodiment of the present invention shown in FIG. 1 and FIG. 3 respectively also lies in the constitution of the sensor portion for detecting the degree of the sympathetic tone. In the equipment of this example, a blood sensor 36 which is formed integrally with the ventricle stimulation/detection electrode 24 or the ventricle electrode-lead 23 arranged in the right ventricle 28 is used. Portions same as those in the block diagrams of FIG. 1 and FIG. 3 are put with the same reference numerals.

In this example, the blood sensor 36 is arranged in the ventricle, but it may be also constituted such that it is constituted integrally with the atrium electrode instead of the ventricle electrode.

The living body information detected by the blood sensor 36 includes a middle cardiac vein blood temperature, a degree of the venous blood oxygen saturation, blood pH, a catecholamine quantity in the blood and the like where either of them relates to the degree of the autonomic tone (especially sympathetic tone) caused by the physical exercise and stress.

The operation of the fourth exemplified embodiment of the heart treatment equipment according to the present invention will be explained hereinafter. The overview explanation of the whole block diagram will be omitted because it is same as that of the first exemplified embodiment shown in FIG. 1. In FIG. 4, the blood sensor 36 is drawn as a separate body with the ventricle stimulation/detection electrode 24 or the ventricle electrode-lead 23 in order to illustrate intelligibly, but it is to be formed as a one body construction therewith in the heart 27.

Information from the blood sensor 36 arranged in this right ventricle 28 is transmitted to the blood information detection unit 37 and is detected with a proper time interval clocked by the blood information detection timer 38. Then, an output of the blood information detection unit 37 is supplied to the heart rate threshold control unit 19 of the control unit 7. Hereinafter, the same operation as the second exemplified embodiment shown in FIG. 3 will be executed.

Figure 5:
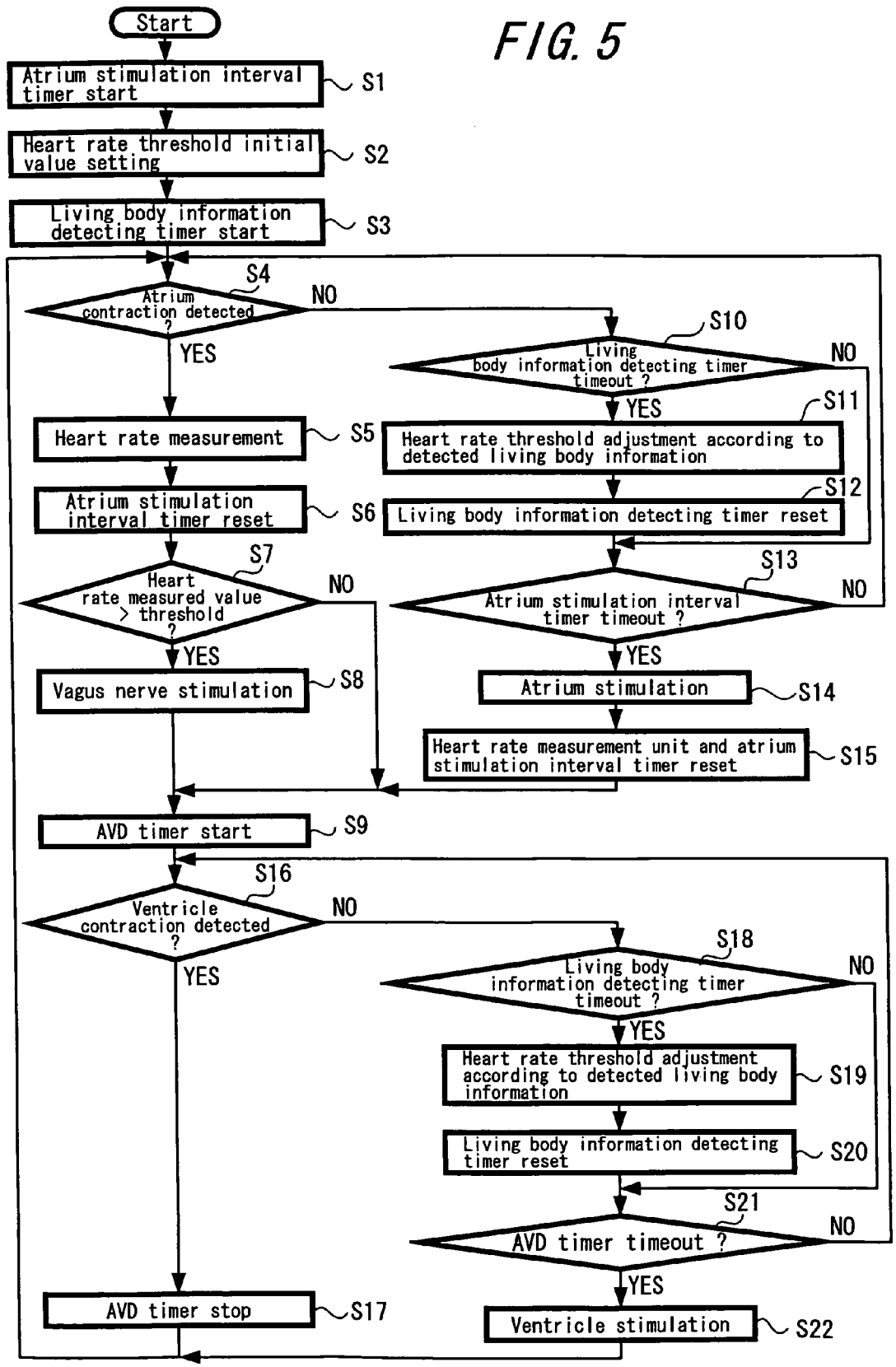
FIG. 5 is a flow diagram showing the operation of the heart treatment equipment of the first to the third exemplified embodiments according to the present invention which are shown in FIG. 1, FIG. 3 and FIG. 4 respectively.

The operations of the first to third exemplified embodiments of the present invention will be explained by using a common flow diagram shown in FIG. 5.

First, the atrium stimulation interval timer 9 is started (step S1). Next, an initial value of a heart rate in the heart rate threshold control unit 19 is set (step S2), further a living body information detecting timer used for various sensors is started (step S3) and initialization of the system is completed. Here, the living body information is body motion in the first exemplified embodiment, is breathing in the second exemplified embodiment and blood in the third exemplified embodiment.

Next, it is judged in the atrium contraction detecting unit 5 whether or not an atrium contraction was detected (step S4). In a case when an atrium contraction was detected in the judgment step S4, a heart rate measurement is started in the heart rate measuring unit 21 (step S5) and at the same time, the atrium stimulation interval timer 9 is reset (step S6).

Next, it is judged whether or not the heart rate measured by the heart rate measuring unit 21 reached the heart rate threshold set in the heart rate threshold control unit 19 (step S7). In a case when it is judged that the heart rate measured value exceeded the threshold set in the aforesaid heart rate threshold control unit 19, an output can be obtained from the heart rate comparator unit 22 and a stimulation of the vagus nerve 32 is carried out by the nerve stimulation unit 6 by way of the nerve stimulation signal control unit 20 (step S8).

In the judgment step S7, when the heart rate measured value of the heart rate measuring unit 21 did not exceed the threshold set in aforesaid heart rate threshold control unit 19, the stimulation of the vagus nerve 32 is not carried out, the output of the atrium contraction detecting unit 5 is applied to the AVD timer 13 by way of the OR circuit 12 and the AVD timer 13 starts clocking (step S9).

Next, in a case when the atrium contraction was not detected in the judgment step S4, it is judged that whether or not the living body information detecting timer was timeout (step S10). When it is judged that the living body information detecting timer was timeout, the heart rate threshold of the heart rate threshold control unit 19 is adjusted to a predetermined value according to the detected living body information (step S11) and at the same time, the living body information detecting timer is reset (step S12). In a case when it is judged the judgment step S10 that the living body information detecting timer was not timeout, the heart rate threshold of the heart rate threshold control unit 19 is not adjusted and the living body information detecting timer is not reset either, so that the flow proceeds to next step S13.

It is judged by the judgment step S13 whether or not the atrium stimulation interval timer 9 was timeout, in other words, whether or not the clocked time of the atrium stimulation interval timer 9 exceeded the set value of the atrium stimulation interval set-value memory unit 10. In a case when the clocked time of the atrium stimulation interval timer 9 exceeded the set value of the atrium stimulation interval set-value memory unit 10, the comparator unit 11 emanates an output and the stimulation of the right atrium 29 is carried out by the atrium stimulation unit 4 (step S14). Also, the output of the comparator unit 11 resets the counted result of the heart rate measuring unit 21, resets the atrium stimulation interval timer 9 by way of the OR circuit 12 (step S15). Then, the AVD timer 13 is also reset and the AVD timer 13 starts clocking (step S9).

In a case when it is judged by the judgment step S13 that the clocked time of the atrium stimulation interval timer 9 did not exceed the set value of the atrium stimulation interval set-value memory unit 10, the flow returns to the judgment step S4 and waits for the detection of the atrium contraction.

Subsequently, it is judged in the ventricle contraction detecting unit 3 whether or not the ventricle contraction was detected (step S16). In a case when the ventricle contraction was detected, the counting of the AVD timer 13 is stopped (step S17), the flow returns to the judgment step S4 and waits for the detection of the next atrium contraction. In a case when the ventricle contraction was not detected in the judgment step S16, it is judged whether or not the living body information detecting timer was timeout (step S18). When it is judged that the living body information detecting timer was timeout, the heart rate threshold of the heart rate threshold control unit 19 is adjusted to a predetermined value according to the detected living body information (step S19) and at the same time, the living body information detecting timer is reset (step S20). In a case when it is judged by the judgment step S18 that the living body information detecting timer was not timeout, the heart rate threshold of the heart rate threshold control unit 19 is not adjusted and the living body information detecting timer is not reset either, so that the flow proceeds to next step S21.

It is judged in the judgment step S21 whether or not the AVD timer 13 was timeout. More specifically, it is judged whether or not the counted value of the AVD timer 13 exceeded a normal atrioventricular delay time set in the AVD set-value memory unit 14 and in case of exceeding it, an output is emanated from the AVD comparator unit 15 and the stimulation of the right ventricle 28 is carried out by the ventricle stimulation unit 2 (step S22). When it is judged in the judgment step S21 that the AVD timer 13 was not timeout, the flow returns to the judgment step S16 and waits for the detection of the ventricle contraction.

As explained above, in the first to third exemplified embodiments of the present invention, states of body motion, breathing and blood are detected and the upper limit heart rate for stimulating the vagus nerve is adjusted according to these of living body information, so that it is possible to carry out the vagus nerve stimulation in an optimum state for a patient and furthermore in a state in which strain is little.

Next, a fourth exemplified embodiment of the present invention will be explained according to a block constitutional diagram of FIG. 6. The same constitutional portions as those in the first to third exemplified embodiments of the present invention (FIG. 1, FIG. 3 and FIG. 4) are shown by putting with the same reference numerals.

Figure 6:
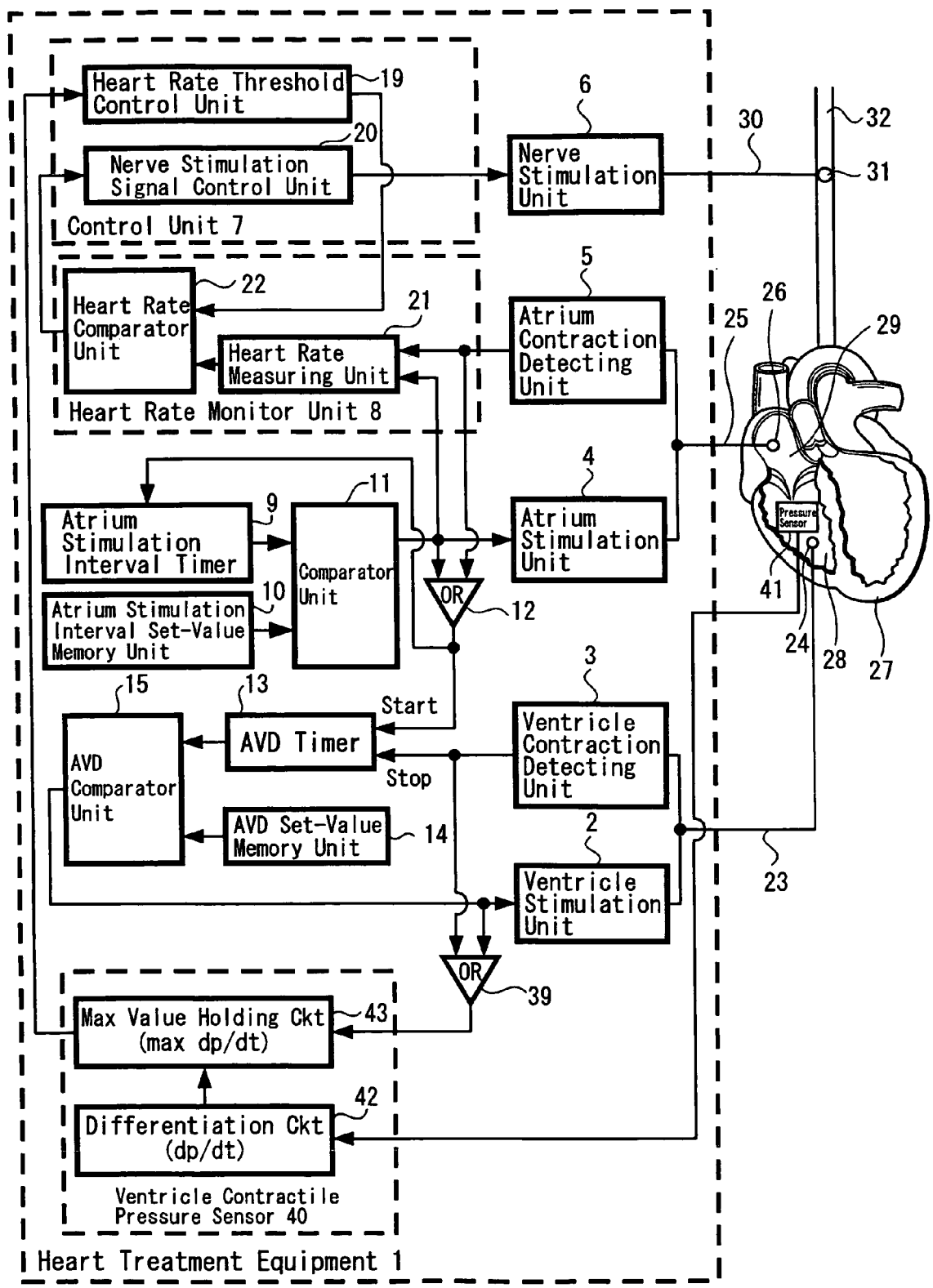
FIG. 6 is a diagram showing a constitutional example of heart treatment equipment of a fourth exemplified embodiment according to the present invention.

The fourth exemplified embodiment of the present invention shown in FIG. 6 is different from the first to third exemplified embodiments in that a ventricle contractile pressure sensor 40 is used as the living body information sensor. As the ventricle contractile pressure sensor 40, it is constituted by a differentiation circuit (dp/dt) 42 for detecting time changing ratio (time differentiation) dp/dt of the pressure in a ventricle, which is detected by a pressure sensor 41 arranged in the ventricle and a max value holding circuit (max dp/dt) 43 for holding a max value of an output of the differentiation circuit 42. Then, an output of the ventricle contraction detecting unit 3 and an output of the AVD comparator unit 15, that is, signal for triggering the ventricle stimulation unit 2 are supplied thereto and an OR circuit 39 is added newly for supplying the outputs to the max value holding circuit (max dp/dt) 43. The max value holding circuit (max dp/dt) 43 starts monitoring the output of the differentiation circuit 42 at the timing of the output from the OR circuit 39 and holds the max value thereof.

Hereinafter, it will be explained with respect to the operation of the fourth exemplified embodiment of the present invention. The pressure sensor 41 is a sensor for measuring the pressure when the ventricle contracts and ordinarily is equipped in the ventricle stimulation/detection electrode 24 or the ventricle electrode-lead 23. Then, the pressure in the ventricle is measured by the pressure sensor 41 and it is transmitted to the differentiation circuit 42. The differentiation circuit 42 differentiates the signal from this pressure sensor 41, obtains dp/dt and supplies it to the max value holding circuit 43. The max value holding circuit 43 holds the max value of the output of the differentiation circuit 42 at an output timing of the OR circuit 39, that is, within a predetermined period from the timing of the ventricular contraction detection or the stimulation of the ventricle, for example, within a period of 100 msec and obtains a max dp/dt.

Then, the held max dp/dt is transmitted to the heart rate threshold control unit 19 of the control unit 7, the heart rate in response to the max dp/dt is determined as a threshold on an occasion when a nerve stimulation is carried out. As the max dp/dt increases according to an intense physical exercise or a mental stress, it is possible to sense from the max dp/dt how much the physical exercise or the mental stress is. Then, it is constituted such that the upper limit heart rate when the nerve stimulation is carried out is made different depending on the occasion when the max dp/dt is large or small.

Figure 7:
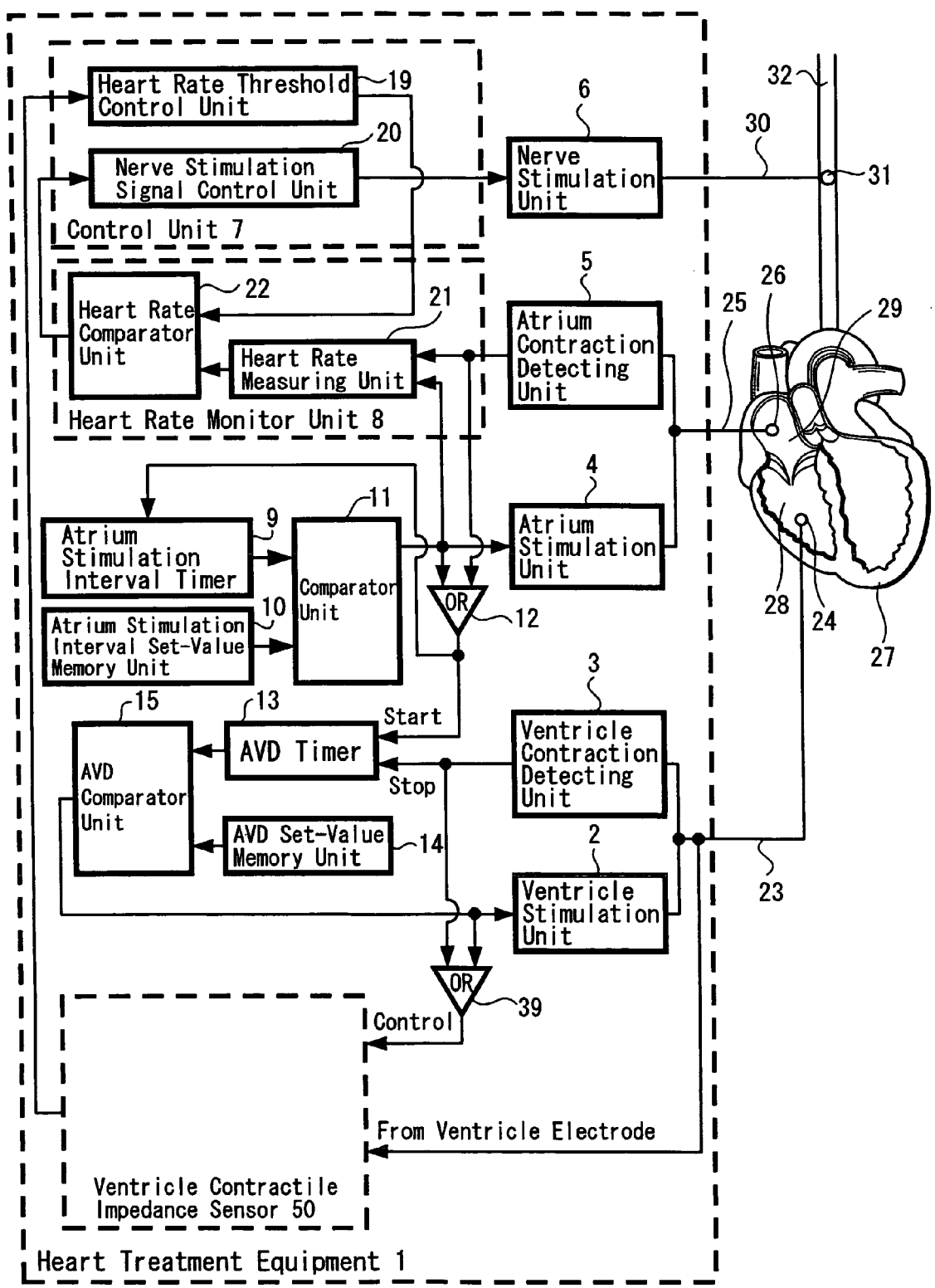
FIG. 7 is a diagram showing a constitutional example of heart treatment equipment of a fifth and a sixth exemplified embodiments according to the present invention.

FIG. 7 is a block constitutional diagram showing a fifth and a sixth exemplified embodiments of the heart treatment equipment according to the present invention. The difference from the fourth exemplified embodiment of FIG. 6 lies in that a ventricle contractile impedance sensor 50 is used as a sensor for detecting the living body information. Other block constitutions are same as those of the fourth exemplified embodiment, so that same reference numerals are put for the same block constitutions.

Figure 8:
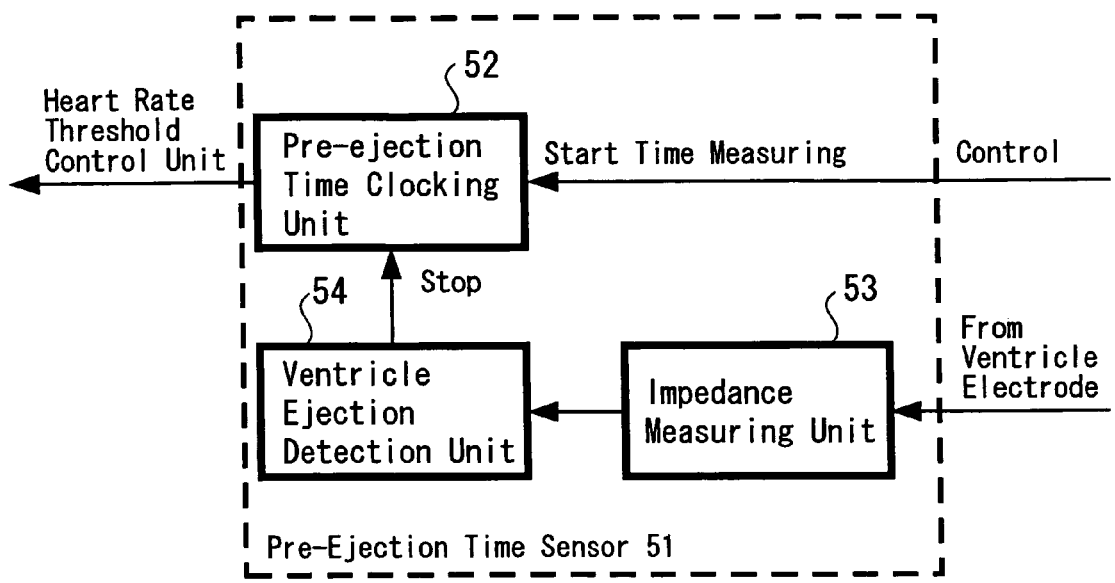
FIG. 8 is a block diagram of a pre-ejection time sensor used as sensor means of the fifth exemplified embodiment according to the present invention.
Figure 9:
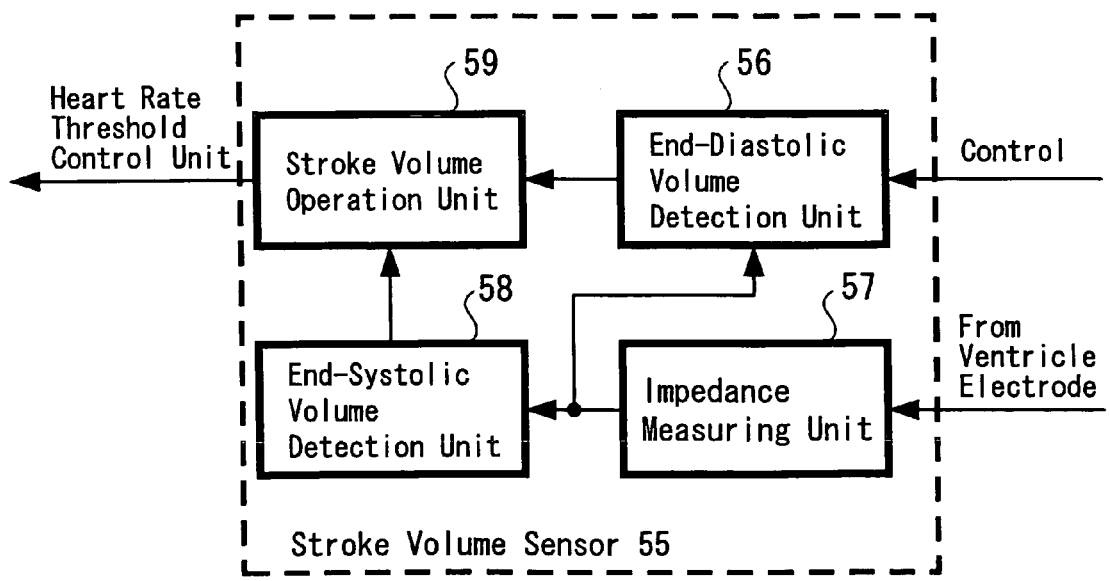
FIG. 9 is a block diagram of a stroke volume sensor used as sensor means the sixth exemplified embodiment according to the present invention.

Embodiments of the ventricle contractile impedance sensor 50 are shown in FIG. 8 and FIG. 9. FIG. 8 shows an embodiment in which a pre-ejection time sensor 51 is used as the ventricle contractile impedance sensor 50 and it will be explained by designating this exemplified embodiment as a fifth exemplified embodiment and by designating the exemplified embodiment using a stroke volume sensor 55 shown in FIG. 9 as a ventricle contractile impedance sensor 50 as a sixth exemplified embodiment of the present invention.

First, the constitution and the operation of the fifth exemplified embodiment according to the present invention will be explained and before that it will be explained with respect to ventricle pre-ejection time. The ventricle pre-ejection time is time after the start of depolarization of the ventricle (ventricle contraction detection or ventricle stimulation) until the ventricle actually starts the blood ejection. It is possible to sense depending on the ventricle pre-ejection time how much a physical exercise or a mental stress is.

The pre-ejection time sensor 51 is constituted by a pre-ejection time clocking unit 52 for starting a time measurement triggered by the ventricle contraction detection or the ventricle stimulation, an impedance measuring unit 53 for monitoring volume change of the ventricle and a ventricle ejection detection unit 54 for receiving an output of the impedance measuring unit 53 and for judging that the blood ejection is started when there is a predetermined decrease in the ventricle volume.

Hereinafter, the operation of the fifth exemplified embodiment will be explained and in FIG. 7, an output of the ventricle contraction detecting unit 3 and an output of the AVD comparator unit 15 are supplied to the OR circuit 39. Consequently, an output is obtained from the OR circuit 39 in a case when the ventricle contraction was detected or in a case when the ventricle stimulation was carried out, this output is supplied to the pre-ejection time clocking unit 52 of the pre-ejection time sensor 51 (FIG. 8) and the measurement of the pre-ejection time is started. Then, the ventricle stimulation/detection electrode 24 is connected to the impedance measuring unit 53 of FIG. 8 through the ventricle electrode-lead 23 and the impedance measuring unit 53 detects the ventricle volume change as an impedance change if there is a change in the ventricle volume.

The output of the impedance measuring unit 53 is transmitted to the ventricle ejection detection unit 54, and the ventricle ejection detection unit 54 monitors the output, that is, impedance change from the impedance measuring unit 53, judges that the blood ejection was started in a case when there is a predetermined decrease in the ventricle volume and stops the clocking of the pre-ejection time clocking unit 52. The ventricle pre-ejection time measured in this manner is transmitted to the heart rate threshold control unit 19 of the control unit 7 in FIG. 7 and the upper limit rate of the heart rate carrying out the nerve stimulation is controlled and also selected in response to the ventricle pre-ejection time.

FIG. 9 is a block diagram showing a constitution of the stroke volume sensor 55 which is a second example of the ventricle contractile impedance sensor 50 shown in FIG. 7.

The stroke volume is a volume subtracting the end-systolic volume from the end-diastolic volume for one heartbeat and it becomes also possible from this stroke volume to know how much is the physical exercise or the mental stress is.

The embodiment where the stroke volume sensor 55 of FIG. 9 is adopted as the ventricle contractile impedance sensor 50 of FIG. 7 is designated as an sixth exemplified embodiment according to the present invention.

The stroke volume sensor 55 shown in FIG. 9 is constituted by end-diastolic volume detection unit 56 for detecting the end-diastolic volume triggered by the ventricle contraction detection or the ventricle stimulation, impedance measuring unit 57 for monitoring the ventricle volume change based on the impedance change, end-systolic volume detection unit 58 for detecting the minimum value of the ventricle volume as a end-systolic volume from the output of the impedance measuring unit 57 subsequent to the end-diastolic volume detection, and stroke volume operation unit 59 for operating the stroke volume of the ventricle by subtracting the output of the end-systolic volume detection unit 58 from the output of the end-diastolic volume detection unit 56.

The operation of the sixth exemplified embodiment according to the present invention will be explained hereinafter, and in FIG. 7, as mentioned above, an output is obtained at the OR circuit 39 when the ventricle contraction is detected or the ventricle stimulation is performed where this output is supplied to the end-diastolic volume detection unit 56 of the stroke volume sensor 55 (FIG. 9). On the other hand, the impedance measuring unit 57 connected to the ventricle stimulation/detection electrode 24 determines the ventricle volume from the measured impedance and this is transmitted to the end-diastolic volume detection unit 56 and the end-systolic volume detection unit 58. The end-diastolic volume detection unit 56 detects the ventricle volume at the time of the ventricle contraction detection or at the time of the ventricle stimulation according to the output of the impedance measuring unit 57 and makes that volume as a end-diastolic volume. Further, the end-systolic volume detection unit 58 monitors the output of the impedance measuring unit 57 and detects the minimum value of the ventricle volume as a end-systolic volume.

Then, in the stroke volume operation unit 59, an output difference between the end-diastolic volume detection unit 56 and the end-systolic volume detection unit 58, that is, the difference between the end-diastolic volume and the end-systolic volume is operated and this operated result is transmitted to the heart rate threshold control unit 19 of the control unit 7 in FIG. 7 as a stroke volume. The heart rate threshold control unit 19 perceives the degree of the sympathetic tone caused by a physical exercise quantity or a mental stress of a patient from this stroke volume information and is to set the upper limit rate of the heart rate for carrying out the nerve stimulation in response thereto.

Figure 10:
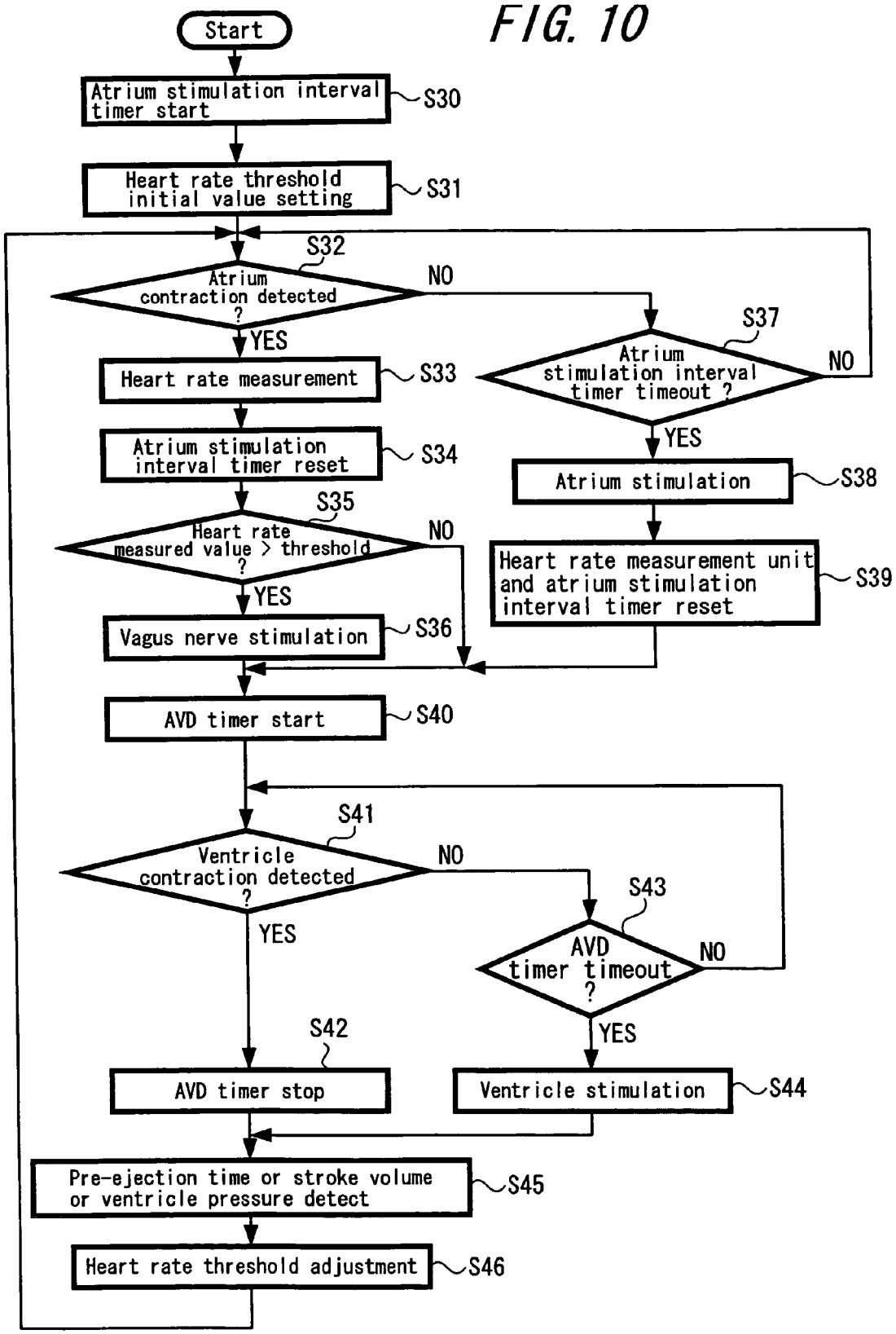
FIG. 10 is a flow diagram showing the operation of the heart treatment equipment of the fourth to the sixth exemplified embodiments according to the present invention which are shown in FIG. 6, FIG. 7, FIG. 8 and FIG. 9.

Next, the operations of the sixth to the eighth exemplified embodiments according to the present invention shown in FIG. 6 to FIG. 9 will be explained in detail using the flow diagram of FIG. 10.

First, at the beginning, the atrium stimulation interval timer 9 is started (step S30) and at the same time, an initial value of the heart rate threshold is set (step S31). Next, it is judged in the atrium contraction detecting unit 5 whether or not an atrium contraction was detected (step S32). When the atrium contraction was detected, the heart rate measurement is started (step S33) and subsequently, the atrium stimulation interval timer 9 is reset so as to start the counting (step S34).

Next, it is judged whether or not the heart rate measured value exceeded the heart rate threshold set in step 31 (step S35) In a case when the heart rate measured by the heart rate measuring unit 21 exceeded the heart rate threshold (initial value) set in the heart rate threshold control unit 19, an output is emanated from the heart rate comparator unit 22 and a stimulation of the vagus nerve 32 is carried out by way of the nerve stimulation signal control unit 20 and the nerve stimulation unit 6 (step S36).

In a case when it is judged in the judgment step S32 that the atrium contraction was not detected, it is judged whether or not the atrium stimulation interval timer 9 was timeout, that is, whether or not the clocked time of the atrium stimulation interval timer 9 exceeded the set value stored in the atrium stimulation interval set-value memory unit 10 (step S37). Then, if it is judged that it was timeout, an output is emanated from the comparator unit 11 to the atrium stimulation unit 4 and the atrium stimulation is carried out (step S38). Also, the counted result of the heart rate measuring unit 21 is reset and at the same time, the atrium stimulation interval timer 9 is reset (through the OR circuit 12) (step S39). When the heart rate measured value did not reach the threshold for stimulating the vagus nerve 32 in the judgment step S35, the flow proceeds to next step S40 without stimulating the vagus nerve 32 and in a case when it is judged by the judgment step S37 that the atrium stimulation interval timer 9 was not timeout, the flow returns to the judgment step S32 and waits for the atrium contraction detection.

When the atrium stimulation was carried out by the output of the comparator unit 11 and when the atrium contraction was detected in the atrium contraction detecting unit 5, the AVD timer 13 starts counting (step S40). Subsequently, it is judged in the ventricle contraction detecting unit 3 whether or not the ventricle contraction was detected (step S41). If the ventricle contraction was detected in the judgment step S41, the counting of the AVD timer 13 is stopped (step S42) and when the ventricular contraction was not detected in the judgment step S41, it is judged whether or not the AVD timer 13 was timeout, that is, whether or not it exceeded the set value stored in the AVD set-value memory unit 14 (step S43). If it is judged in the judgment step S43 that it was timeout, an output is emanated from the AVD comparator unit 15 to the ventricle stimulation unit 2 and the ventricle stimulation is carried out (step S44).

When this ventricle stimulation was carried out and when the ventricle contraction was detected and the clocking of the AVD timer 13 is stopped in step S42, detections of the ventricle pressure (fourth exemplified embodiment), the pre-ejection time (fifth exemplified embodiment) and the stroke volume (sixth exemplified embodiment) are carried out depending on the sensor means of the respective exemplified embodiments (step S45). Then, the living body information relating to the physical exercise or the mental stress which was detected by the sensor means of respective embodiments is transmitted to the heart rate threshold control unit 19 of the control unit 7 and the threshold is adjusted to an optimum heart rate threshold depending on the patient (step S46).

Figure 11:
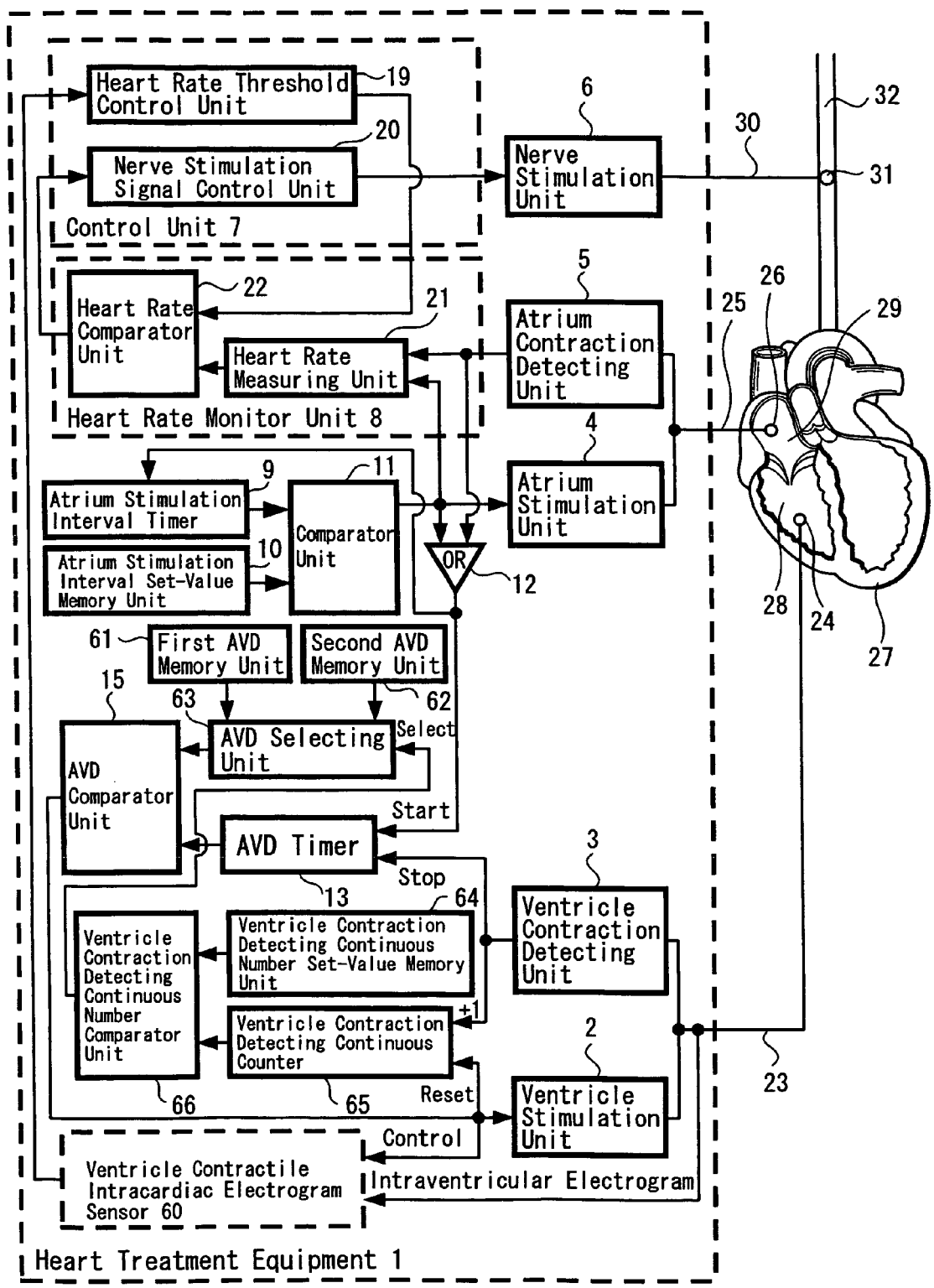
FIG. 11 is a diagram showing a constitutional example of heart treatment equipment of a seventh and an eighth exemplified embodiments according to the present invention.

FIG. 11 is a block constitutional diagram showing a seventh and a eighth exemplified embodiments of the present invention. In FIG. 11, a mode adopting a QT time sensor 70 shown in FIG. 12 as a ventricle contractile intracardiac electrogram sensor 60 is designated as a seventh exemplified embodiment and a mode adopting an intraventricular electrogram area sensor 75 shown in FIG. 13 is designated as an eighth exemplified embodiment, and hereinafter, explanation thereof will be carry out.

In the exemplified embodiment in FIG. 11, the constitution different from those of the first to sixth exemplified embodiments shown in FIG. 1, FIG. 3, FIG. 4, and FIGS. 6 to 9 lies in that the ventricle contractile intracardiac electrogram sensor 60 is used and there are provided two kinds of set values of the AVD (atrioventricular delay time) so as to change over. More specifically, in the seventh and eighth exemplified embodiments shown in FIG. 11, there are added with the ventricle contractile intracardiac electrogram sensor 60 for detecting living body information of a patient from intraventricular electrogram information, a ventricle contraction detecting continuous counter 65 connected to the ventricle stimulation unit 2 and the ventricle contraction detecting unit 3, a ventricle contraction detecting continuous number set-value memory unit 64, a ventricle contraction detecting continuous number comparator unit 66 supplied with outputs of the ventricle contraction detecting continuous counter 65 and the ventricle contraction detecting continuous number set-value memory unit 64, a first AVD memory unit 61 for storing a first AVD set value which is a atrioventricular delay time at the time of normal, a second AVD memory unit 62 for storing a second AVD set value which is shorter than the atrioventricular delay time at the time of normal and an AVD selecting unit 63 for selecting either one of the first AVD memory unit 61 and the second AVD memory unit 62.

Figure 12:
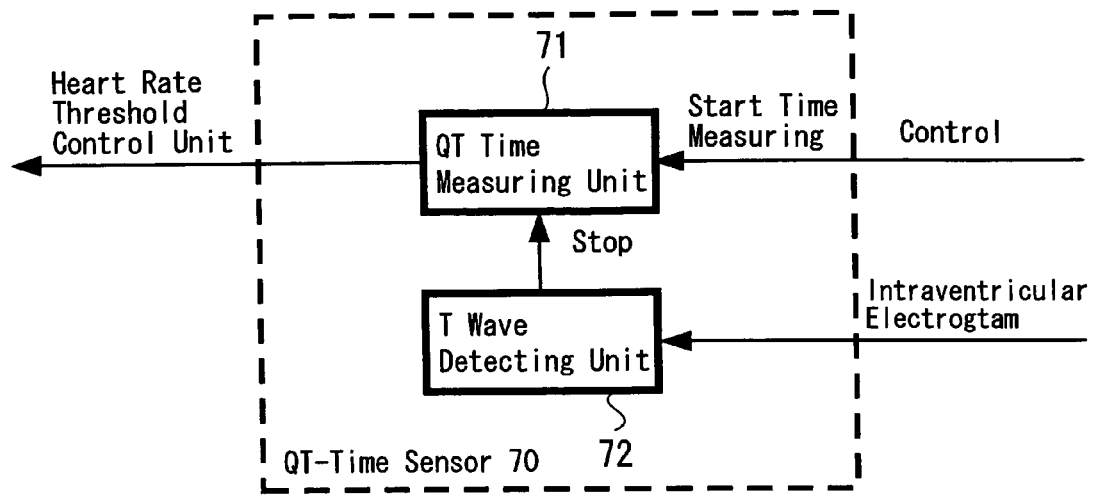
FIG. 12 is a block diagram of a QT time sensor used as sensor means of the seventh exemplified embodiment according to the present invention.

Then, the QT time sensor 70 which is used as one exemplified embodiment of the ventricle contractile intracardiac electrogram sensor 60 is shown in FIG. 12 and the constitution thereof is constituted by QT time measuring unit 71 supplied with an output of the AVD comparator unit 15 shown in FIG. 11 and T-wave detecting unit 72 for detecting a T-wave from an intraventricular electrogram where the intraventricular electrogram is supplied from the ventricle detection electrode 24 only when the ventricle stimulation is performed. The output of this T-wave detecting unit 72 is supplied to the QT time measuring unit 71 and the QT time is measured so as to be supplied to the heart rate threshold control unit 19 of the control unit 7 shown in FIG. 11.

Figure 13:
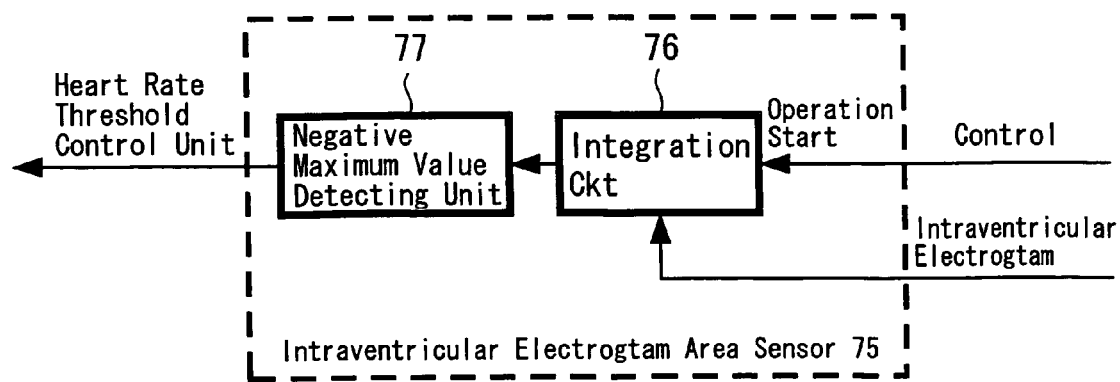
FIG. 13 is a block diagram of an intraventricular electrogram area sensor used as sensor means of the eighth exemplified embodiment according to the present invention.

Further, an intraventricular electrogram area sensor 75 shown in FIG. 13 is also used as one of the ventricle contractile intracardiac electrogram sensor 60. The intraventricular electrogram area sensor 75 is constituted by an integration circuit 76 supplied with an intraventricular electrogram from the ventricle detection electrode 24 and an output of the AVD comparator unit 15; and a negative maximum value detecting unit 77 for detecting a negative max value of the output of the integration circuit 76.

Figure 20A:
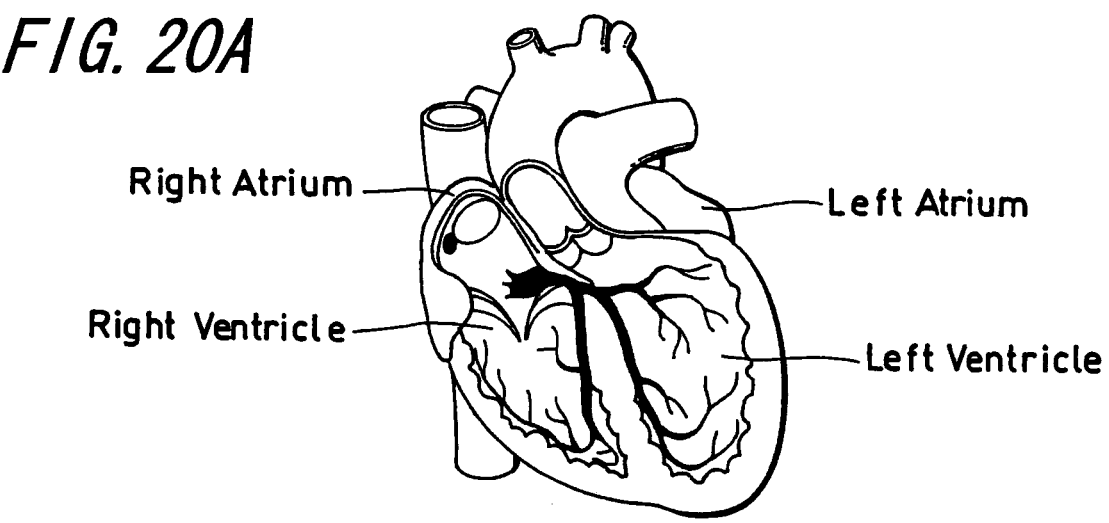
FIG. 20A is a diagram showing a heart construction and FIG. 20B is an example of a surface electrocardiogram.
Figure 20B:
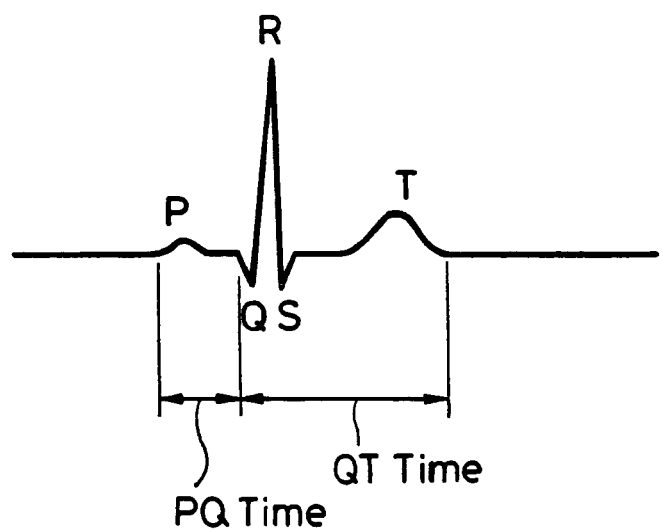

Here, it is to be explained with respect to the QT time measurement by using the intraventricular electrogram shown in FIG. 14. This intraventricular electrogram is slightly different from a surface electrocardiogram which is shown in FIG. 20B. More specifically, P-wave for observing the atrium contraction seldom or never exists on the intraventricular electrogram and the intraventricular electrogram is constituted by QRS-wave which starts from the ventricle stimulation and T-wave which is different from the QRS-wave in polarity. T-wave is a wave emanated when the ventricle relaxes, that is, when the ventricle excitement ends.

As already explained, the QT time is a time after a time point when the right ventricle is stimulated and the ventricles are depolarized until the ventricles are repolarized so as to return to an normal condition. When the QT time is measured by using the intraventricular electrogram, time differentiation of the T-wave is conducted and the QT time is measured by setting a T point which is a point when the differentiated value (inclination) becomes a negative maximum value. This QT time is living body information relating to a representative ventricle contractile and is around 400 ms on a usual condition, that is, at the time of normal, but the QT time becomes shorter less than a half at the time of normal when the sympathetic tone is accentuated in case of an intense physical exercise or a stress felt.

Figure 14A:
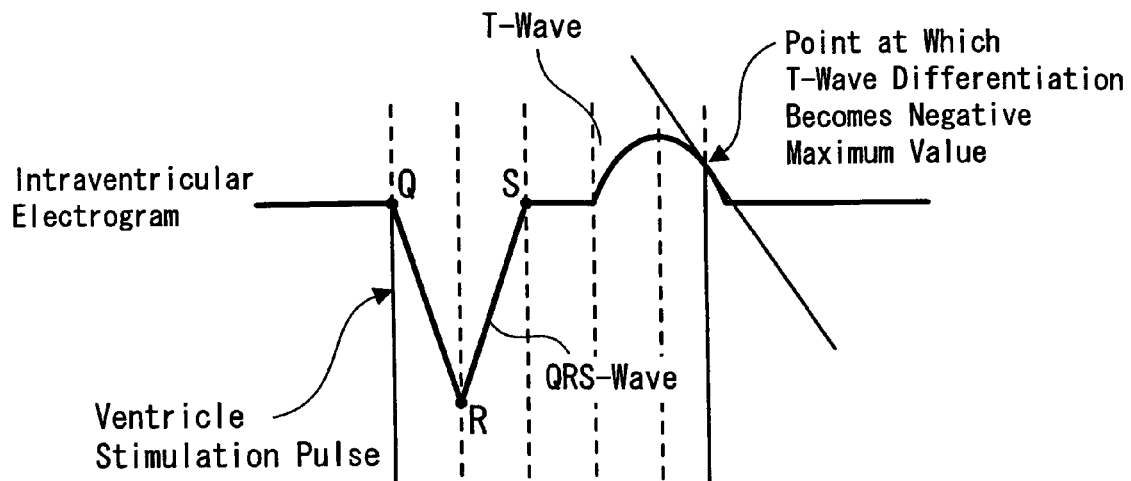
FIG. 14A is a waveform diagram showing an intraventricular electrogram of the heart and QT time.
Figure 14B:
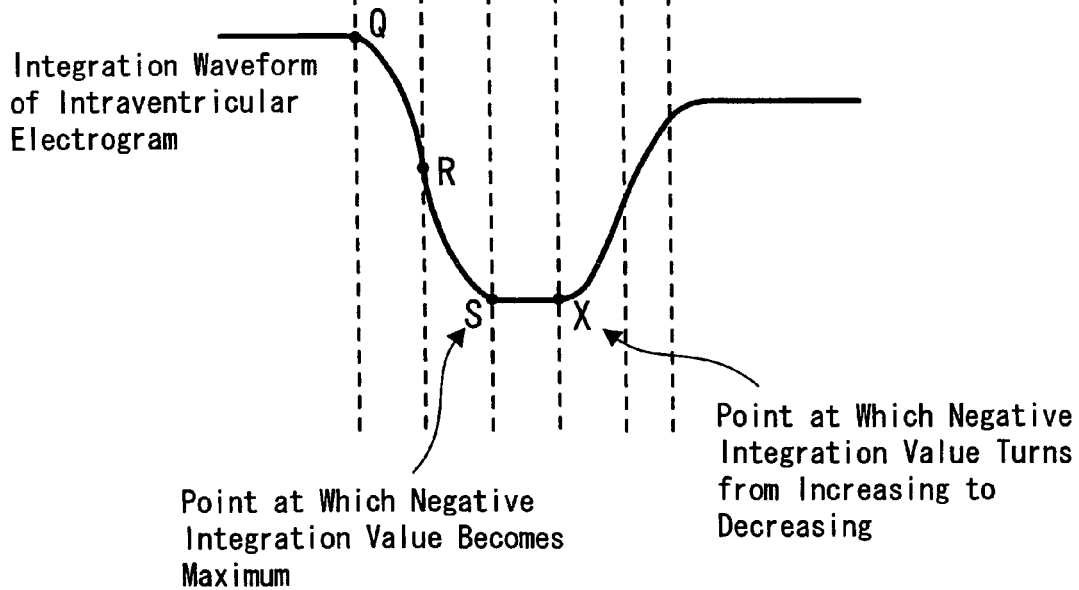
FIG. 14B is a waveform diagram obtained by integrating the intraventricular electrogram.

The waveform diagram shown in FIG. 14B is a waveform diagram obtained by integrating the intraventricular electrogram shown in FIG. 14A in the integration circuit 76 of the intraventricular electrogram area sensor 75 (FIG. 13). As clear by FIG. 14B, when the QRS-wave (negative polarity) is integrated from a Q point of a predetermined potential which is a reference potential, the value of the negative area increases monotonously, but aforesaid negative integrated value turns to a decreasing direction at the stage of integrating the T-wave, because the T-wave has an opposite (positive) polarity with respect to the QRS-wave. The intraventricular electrogram area has a negative maximum value corresponding to a value on a line from a point S when the integration of the QRS-wave is finished to a time point (tentatively named as "X") when the detection of the T-wave starts. The negative maximum value detecting means 77 detects aforesaid value and transmits this negative integrated maximum value to the heart rate threshold control unit 19 of the control unit 7 in FIG. 11 as living body information.

Hereinafter, the operation of the seventh exemplified embodiment will be explained in a case when the QT time sensor 70 shown in FIG. 12 is adopted as the ventricle contractile intracardiac electrogram sensor 60 of FIG. 11. Repetitions of the explanations with respect to the operations of the first to sixth exemplified embodiments which were already explained will be omitted.

First, when a contraction of the right atrium 29 is detected by the atrium contraction detecting unit 5, the atrium contraction detecting unit 5 transmits its output to the AVD timer 13 through the OR circuit 12 such that the counting operation of the AVD timer 13 is started.

In an initial condition, the AVD selecting unit 63 selects an AVD (atrioventricular delay time) set-value at the time of normal, for example, 150 ms which is stored in the first AVD memory unit 61. In a normal heart condition, a spontaneous ventricle contraction occurs before counting the set-value stored in the first AVD memory unit 61 after the AVD timer 13 starts, so that the AVD timer 13 is stopped every at that time by the output of the ventricle contraction detecting unit 3. Consequently, the AVD timer 13 will not be counted up to the set-value stored in the first AVD memory unit 61 which is selected by the AVD selecting unit 63. Therefore, in this case, an output cannot be obtained from the AVD comparator unit 15 and the ventricle stimulation unit 2 is not supplied with an output of the AVD comparator unit 15, so that it does not happen that a ventricle stimulation is performed.

If it is a case that a spontaneous ventricle contraction does not occur within the atrioventricular delay time at the time of normal which is stored in the first AVD memory unit 61, an output cannot be obtained from the ventricle contraction detecting unit 3, so that the AVD timer 13 does not stop and continues counting. More specifically, the AVD timer 13 continues counting until it becomes in conformity to the set-value stored in the first AVD memory unit 61 which is selected by the AVD selecting unit 63 and generates an output from the AVD comparator unit 15 at the time point in conformity thereto.

The output of the AVD comparator unit 15 is transmitted to the ventricle stimulation unit 2 and the stimulation of the right ventricle 28 is performed by the ventricle stimulation electrode 24 through the ventricle electrode-lead 23. At the same time, the output of the AVD comparator unit 15 is added to the ventricle contraction detecting continuous counter 65 and resets the ventricle contraction detecting continuous counter 65. In addition, the output of the AVD comparator unit 15 is supplied to the QT time measuring unit 71 of the QT time sensor 70 shown in FIG. 12 and the QT time measuring unit 71 is made to start.

On the other hand, the ventricle contraction detecting continuous counter 65 is increment every time when an spontaneous ventricle contraction is detected by the ventricle contraction detecting unit 3, an output is generated from the ventricle contraction detecting continuous number comparator unit 66 when the ventricle contraction is continuously detected until the number of times (specifically, around 3 to 10 times) which is stored in the ventricle contraction detecting continuous number set-value memory unit 64. The output of this ventricle contraction detecting continuous number comparator unit 66 is supplied to the AVD selecting unit 63. The AVD selecting unit 63 changes its set-value from the set-value of the first AVD memory unit 61 to the set-value of the second AVD memory unit 62 in response to the output of the ventricle contraction detecting continuous number comparator unit 66.

The set-value stored in this second AVD memory means 62 is selected shorter than about 150 ms which is the AVD (atrioventricular delay time) at the time of normal and, for example, is selected to be 100 ms. Here, when it is assumed that set-value is 100 ms of the AVD time, the ventricle contraction is not detected by the ventricle contraction detecting unit 3 during when the AVD timer 13 counts 100 ms, so that the AVD timer 13 always counts the set-value stored in the second AVD memory unit 62 such that an output is obtained from the AVD comparator unit 15 every time.

The output of this AVD comparator unit 15 is added to the ventricle stimulation unit 2, the ventricle contraction detecting continuous counter 65 and QT time measuring unit 71 (FIG. 12). Then, the measurement of the QT time as living body information which expresses the degree of the sympathetic tone is conducted. Here, it is because the ventricle stimulation should be compulsorily performed in the AVD selecting unit 63 in order to switch the AVD time set-value from the first AVD memory unit 61 to the second AVD memory unit 62 and in order to measure the QT time.

The T-wave detecting unit 72 of the QT time sensor 70 shown in FIG. 12 is designed such that the T-wave is detected only when the right ventricle 28 is stimulated compulsorily, so that when the T-wave is detected, an output thereof is transmitted to the QT time measuring unit 71 and the counting operation of the QT time measuring unit 71 stops. Then, the measured QT time is transmitted from the QT time measuring unit 71 to the heart rate threshold control unit 19 of FIG. 11 and is adjusted to a heart rate threshold in response to the QT time of a patient.

An example of heart rate thresholds in response to this QT time is shown in FIG. 15. In this drawing, in a case when the QT time is 90% or more of an ordinary case, the heart rate threshold is designated as 100 times/min and the heart rate threshold is made fewer as the QT time becomes shorter. In other words, in a case when the QT time is short, the degree of the sympathetic tone becomes high that much, so that it is constituted such that the heart rate threshold stimulating the vagus nerve is to be lowered.

Next, the operation of the seventh exemplified embodiment according to the present invention will be explained in detail by using a flow diagram of FIG. 16. First, the atrium stimulation interval timer 9 is started (step S50) and at the same time, an initial value of the heart rate threshold in the heart rate threshold control unit 19 is set (step S51). Then, the ventricle contraction detecting continuous counter 65 is reset (step S52) and the initialization of the whole system is completed.

Next, it is judged in the atrium contraction detecting unit 5 whether or not an atrium contraction was detected (step S53). When the atrium contraction was detected in the judgment step S53, a signal from the atrium contraction detecting unit 5 is supplied to the heart rate measuring unit 21 and a heart rate measurement is carried out (step S54). Further, the output of the atrium contraction detecting unit 5 is also supplied to the atrium stimulation interval timer 9 by way of the OR circuit 12 and the atrium stimulation interval timer 9 is reset (step S55).

Subsequently, it is judged whether or not the heart rate measured value exceeded the heart rate threshold set in step 51 (step S56). In a case when the heart rate measured by the heart rate measuring unit 21 exceeded the heart rate threshold (initial value) set in the heart rate threshold control unit 19, an output is emanated from the heart rate comparator unit 22 and a stimulation of the vagus nerve 32 is carried out by way of the nerve stimulation signal control unit 20 and the nerve stimulation unit 6 (step S57).

In a case when it is judged in the judgment step S53 that the atrium contraction was not detected, it is judged whether or not the atrium stimulation interval timer 9 was timeout, that is, whether or not the clocked time of the atrium stimulation interval timer 9 exceeded the set value stored in the atrium stimulation interval set-value memory unit 10 (step S58). Then, if it is judged that it was timeout, an output is emanated from the comparator unit 11 to the atrium stimulation unit 4 and the atrium stimulation is carried out (step S59) and also, the heart rate measuring unit 21 is reset and at the same time, the atrium stimulation interval timer 9 is also reset (through the OR circuit 12) (step S60).

When the heart rate measured value did not reach the threshold for stimulating the vagus nerve 32 in the judgment step S56, the flow proceeds to next step S61 without stimulating the vagus nerve 32 and in a case when it is judged by the judgment step S58 that the atrium stimulation interval timer 9 was not timeout, the flow returns to the judgment step S53 and waits for the atrium contraction detection. Then, when the atrium stimulation was carried out by the output of the comparator unit 11 and when the atrium contraction was detected in the atrium contraction detecting unit 5, the AVD timer 13 starts counting (step S61).

It is judged whether or not the ventricle contraction detecting continuous counter 65 reached the set value stored in the ventricle contraction detecting continuous number set-value memory unit 64, that is, whether or not the ventricle contraction was continuously detected as much as the number of 3 to 10 times which is stored in the ventricle contraction detecting continuous number set-value memory unit 64 (step S62). In a case when the counted value of the ventricle contraction detecting continuous counter 65 reached aforesaid set value, an output is applied from the ventricle contraction detecting continuous number comparator unit 66 to the AVD selecting unit 63 and the AVD selecting unit 63 selects the set value stored in the second AVD memory unit 62 (step S63). Since the AVD set value stored in the second AVD memory unit 62 is set more shortly than an ordinary value, the AVD timer 13 reaches the set value of aforesaid second AVD memory unit 62 before the ventricle contraction detecting unit 3 detects a spontaneous ventricle contraction, so that an output is obtained from the AVD comparator unit 15, a compulsory ventricle stimulation is carried out and at the same time, the ventricle contraction detecting continuous counter 65 is reset (step S64). When it is judged in the judgment step S62 that the counted value of the ventricle contraction detecting continuous counter 65 did not reach the set value stored in the ventricle contraction detecting continuous number set-value memory unit 64, the set value stored in the first AVD memory unit 61 is maintained (step S65) and the flow proceeds to next step.

Subsequently, it is judged in the ventricle contraction detecting unit 3 whether or not the ventricle contraction was detected (step S66). If the ventricle contraction was detected in the judgment step S66, the counting of the AVD timer 13 is stopped (step S67) and at the same time, the ventricle contraction detecting continuous counter 65 is incremented (step S68). In a case when it is judged in the judgment step S66 that the ventricle contraction was not detected, it is judged whether or not the AVD timer 13 was timeout, that is, whether or not the counted value of the AVD timer 13 exceeded the set value of the first AVD memory unit 61 or the second AVD memory unit 62 which the AVD selecting unit 63 selects (step S69).

In a case when is judged in the judgment step S69 that the AVD timer 13 was not timeout, the flow returns to the judgment step S66 and waits for the ventricle contraction detection, but in a case when the AVD timer 13 was timeout, an output is emanated from the AVD comparator unit 15 and the ventricle stimulation from the ventricle stimulation unit 2 is carried out (step S70), at the same time, the ventricle contraction detecting continuous counter 65 is reset (step S71) and further, the counting of the QT time measuring unit 71 is started (step S72).

In this state, in a T-wave detecting unit 72 of the QT time sensor 70, time differentiation of the intraventricular electrogram is carried out within a predetermined period corresponding to the T-wave portion and a time point at which the negative inclination becomes maximum is detected from the differentiation waveform (step S73), and the clocking of the QT time measuring unit 71 is stopped (step S74). When the negative maximum value of the T-wave differentiation is detected and the QT time of the intraventricular electrogram is measured, the measured value is transmitted to the heart rate threshold control unit 19 of the control unit 7 in FIG. 11 and the upper limit rate of the heart rate threshold for stimulating the vagus nerve 32 is adjusted (step S75).

Figure 17:
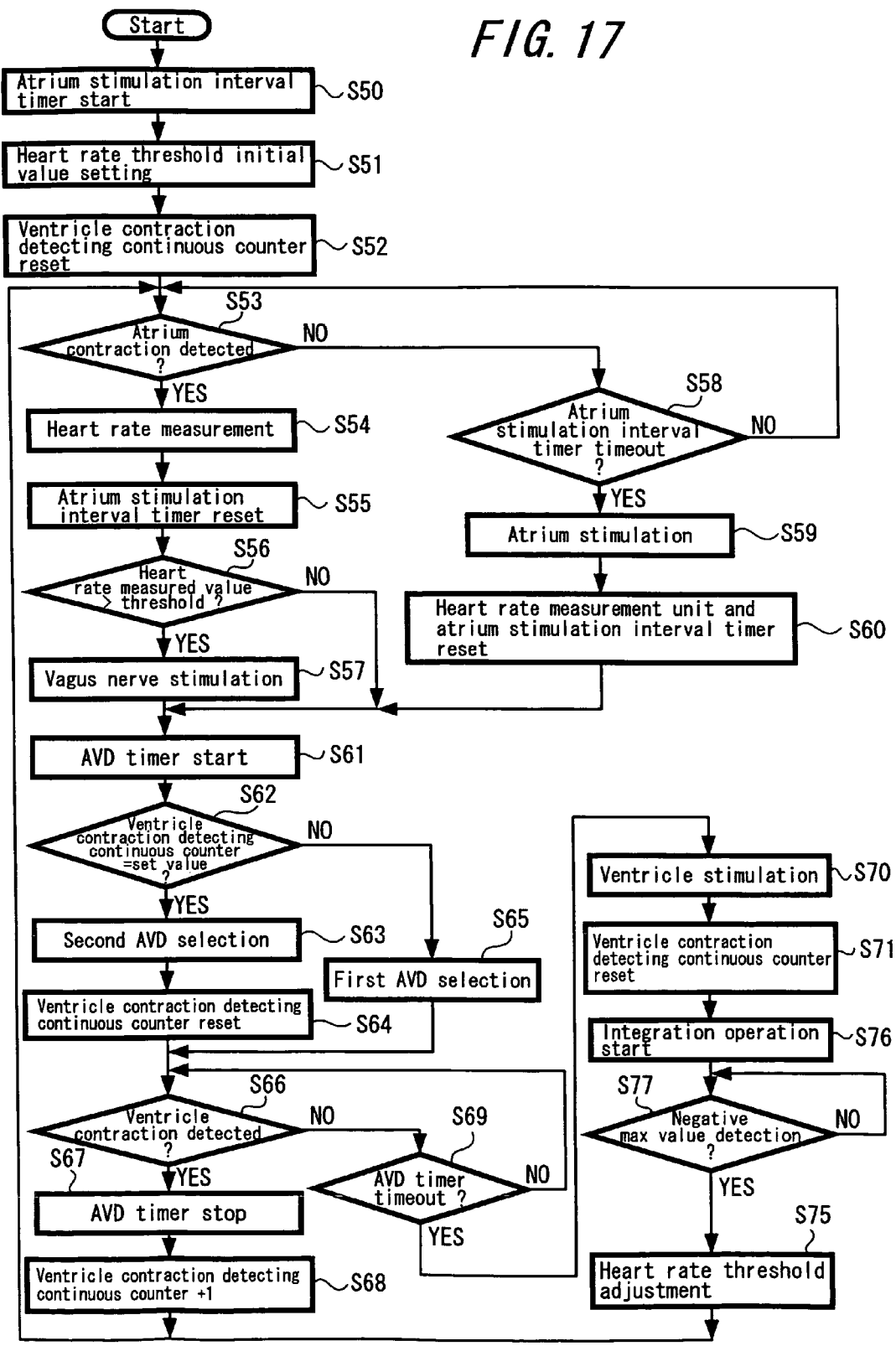
FIG. 17 is a flow diagram showing the operation of the heart treatment equipment of the eighth exemplified embodiment according to the present invention which is shown in FIG. 11 and FIG. 13.

Next, the heart treatment equipment which uses the intraventricular electrogram area sensor 75 shown in FIG. 13 as the ventricle contractile intracardiac electrogram sensor 60 of the exemplified embodiment in FIG. 11 is designated as the eighth exemplified embodiment of the present invention and the operation thereof will be explained according to FIG. 17.

Figure 16:
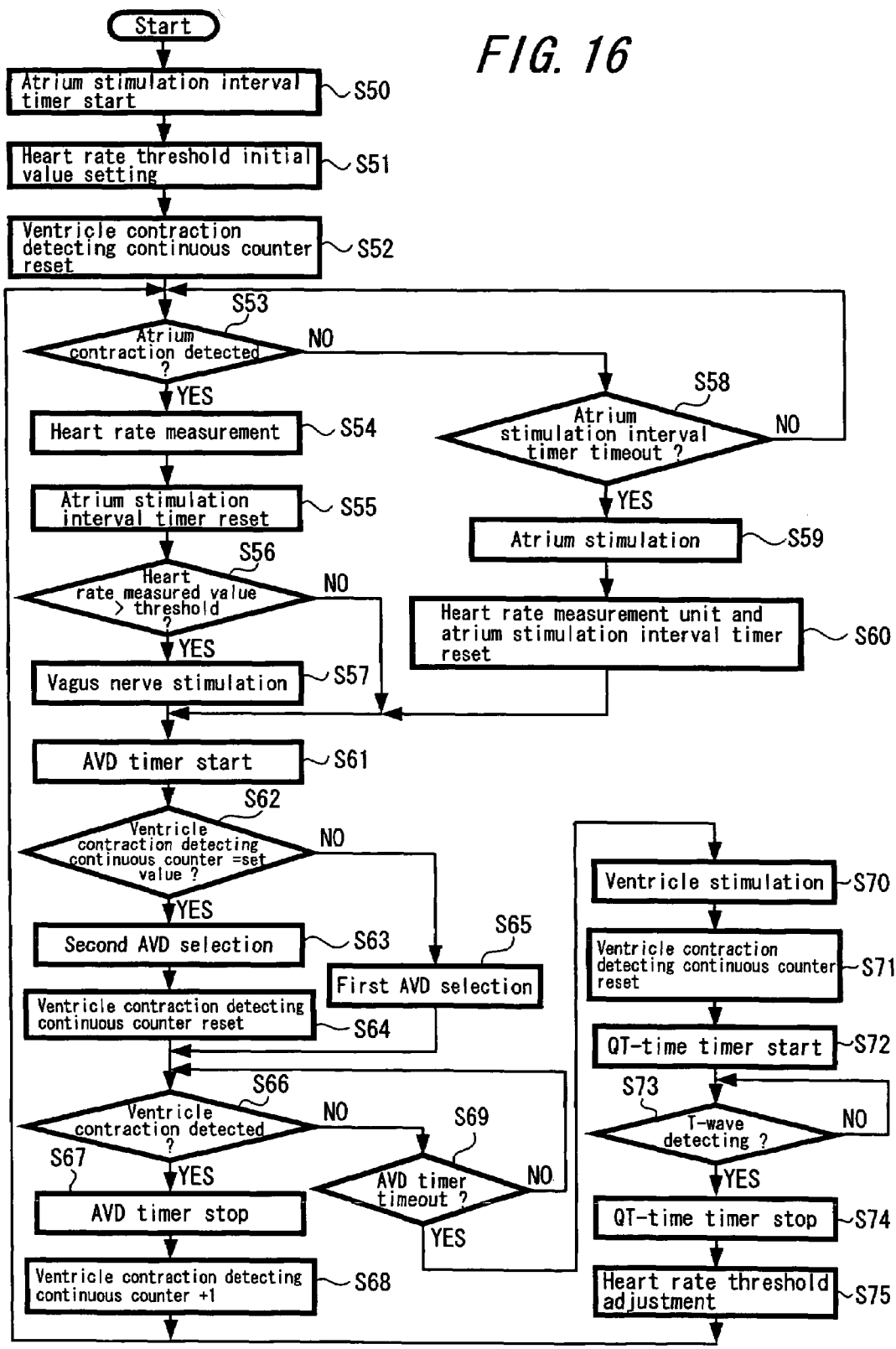
FIG. 16 is a flow diagram showing the operation of the heart treatment equipment of the seventh exemplified embodiment according to the present invention which is shown in FIG. 11 and FIG. 12.

Step S50 to step S71 and step S75 in FIG. 16 are repetitions of the explanation about FIG. 16, so that they are shown by the same reference numerals and the explanation thereof is omitted.

As mentioned above, when the AVD timer 13 was timeout and an output was emanated from the AVD comparator unit 15 in the judgment step S69, the ventricle stimulation from the ventricle stimulation unit 2 is carried out (step S70), and also, the ventricle contraction detecting continuous counter 65 is reset (step S71).

In the eighth exemplified embodiment of the present invention, the intraventricular electrogram area sensor 75 is used as detecting means of the living body information and after aforesaid ventricle stimulation is carried out, an integration operation of the intraventricular electrogram is carried out in the integration circuit 76 of the intraventricular electrogram area sensor 75 (step S76).

At that time, the intraventricular electrogram swings to minus direction from the base potential as shown in FIG. 14A, so that the result of the integration operation is detected as a negative signal output. Next, it is judged whether or not the negative maximum value was detected (step S77) and in a case when it is judged that the negative maximum value was detected, it is constituted such that an output is transmitted to the heart rate threshold control unit 19 in FIG. 11 in response to the negative maximum value and the heart rate threshold when the vagus nerve 32 is stimulated is to be adjusted (step S75).

Figure 18:
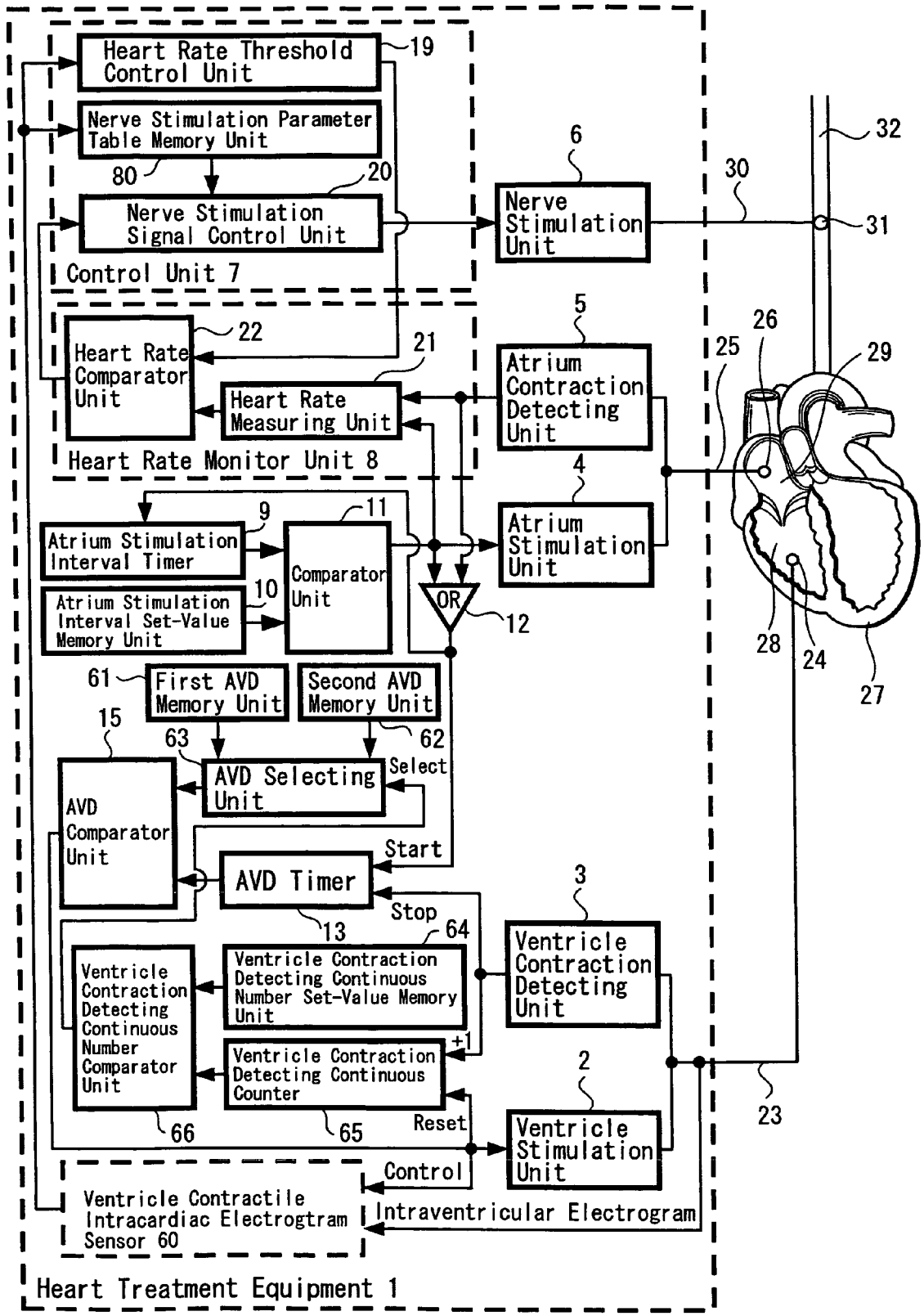
FIG. 18 is a diagram showing a constitutional example of heart treatment equipment of a ninth exemplified embodiment according to the present invention.

FIG. 18 is a block constitutional diagram showing a ninth exemplified embodiment of the heart treatment equipment according to the present invention. The difference from those of the block constitutional diagrams of the seventh and the eighth exemplified embodiments according to the present invention shown in FIG. 11 to FIG. 13 lies in that the output of the ventricle contractile intracardiac electrogram sensor 60 is supplied not only to the heart rate threshold control unit 19 but also to a nerve stimulation parameter table memory unit 80. The same portions as those of the block diagram in FIG. 11 are shown by putting the same reference numerals thereto.

Also in the ninth exemplified embodiment shown in FIG. 18, the QT time sensor 70 and the intraventricular electrogram area sensor 75 shown in FIG. 12 and FIG. 13 respectively are used as the ventricle contractile intracardiac electrogram sensor 60. In this example, it will be explained as an example using the QT time sensor 70, but it is needless to say that the intraventricular electrogram area sensor 75 may be used similarly as a case of FIG. 11.

As shown in FIG. 18, the output of the ventricle contractile intracardiac electrogram sensor 60 is supplied to the heart rate threshold control unit 19 and the nerve stimulation parameter table memory unit 80. In a case when the QT time sensor 70 is used as the ventricle contractile intracardiac electrogram sensor, the QT time measured on an occasion of the ventricle contraction is transmitted to the heart rate threshold control unit 19 and the nerve stimulation parameter table memory unit 80. This QT time, as already explained, has a close relation with the degree of the patient sympathetic tone, so that a parameter, for example, a period between pulses, a pulse width, a number of pulses, a pulse voltage, a pulse current, a delay time, a rest time and a repetitive number or a proper combination chosen from these which carries out a nerve stimulation in response to the QT time is to be determined. More specifically, in a case when it is judged by the measured QT time that the sympathetic tone is intense, it is constituted expecting a stronger prevention effect such that a stimulation parameter value for strengthening the vagus nerve excitement or a certain combination is to be selected.

According to this example, the nerve stimulation parameter is controlled in response to the living body information of aforesaid QT time or the like and at the same time, it is possible to adjust the heart rate threshold which carries out the vagus nerve stimulation in response to the living body information, so that it is possible to carry out the nerve stimulation delicately in response to the patient state.

Figure 19:
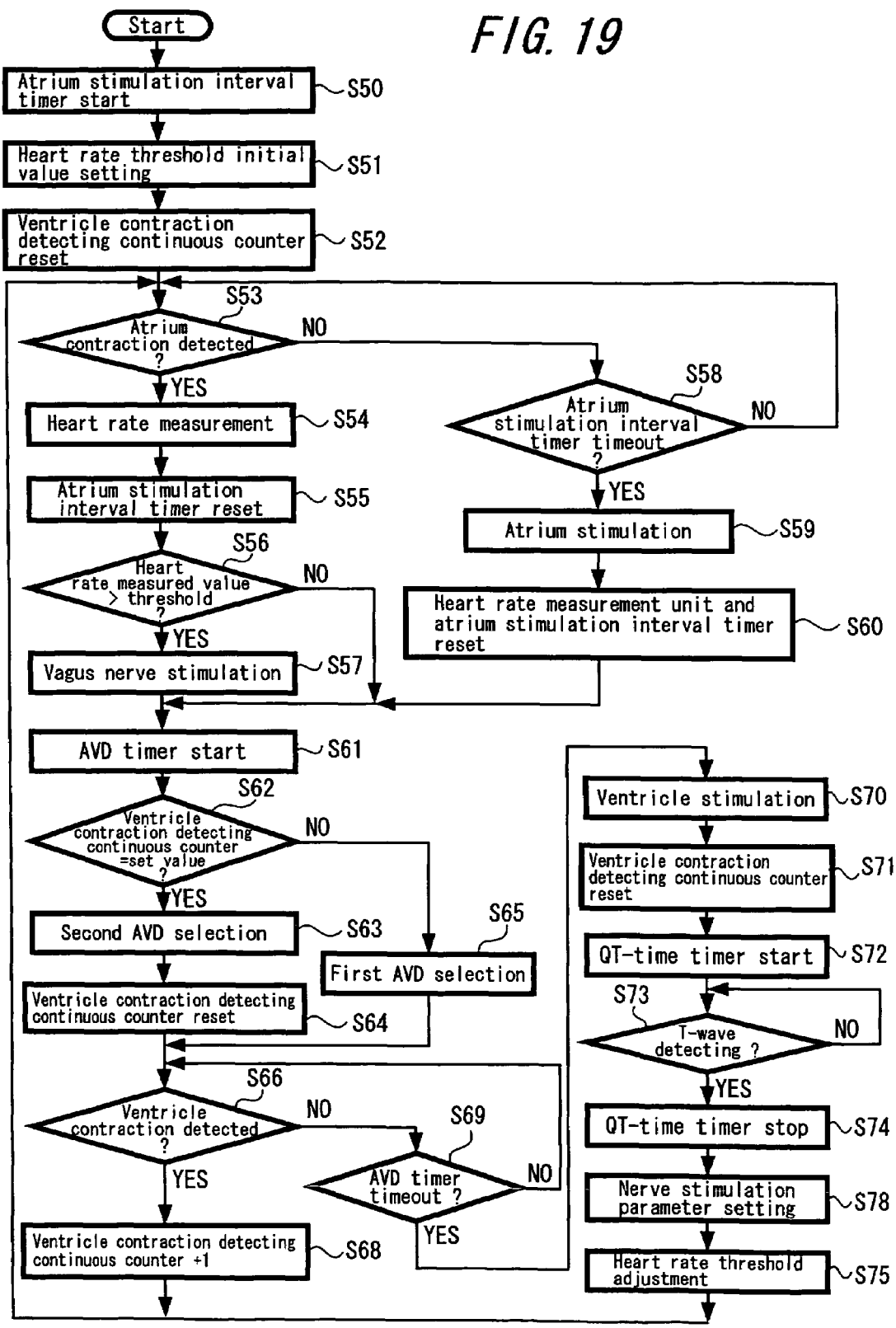
FIG. 19 is a flow diagram showing the operation of the heart treatment equipment of the ninth exemplified embodiment according to the present invention which is shown in FIG. 18.

FIG. 19 is a flow diagram to be used for explaining the ninth exemplified embodiment shown in FIG. 18. It is approximately the same as the flow diagram of FIG. 16 and the difference lies in that step S78 for setting a nerve stimulation parameter is added between step S74 (QT-time timer stop) and step S75 (heart rate threshold adjustment).

In this manner, it becomes possible for the ninth exemplified embodiment of the present invention to adjust the heart rate threshold (upper limit rate) on an occasion when the vagus nerve is stimulated in response to the patient living body information and to select a period between the pulses, a pulse width, a number of pulses, a pulse voltage, a pulse current, a delay time, a rest time, a repetitive number of times or the like delicately on an occasion of a nerve stimulation.

It should be noted that the nerve stimulation parameter control is not limited to a control using a ventricle contractile intracardiac electrogram sensor and it can be realized in the first to sixth exemplified embodiments similarly as this example by supplying each sensor output to the nerve stimulation parameter table memory unit.

As described above, the heart treatment equipment of the present invention was explained with respect to a plurality of exemplified embodiments from first to ninth according to their block diagrams and flow diagrams, but the present invention is not limited by these exemplified embodiments and it is possible to carry out the heart rate threshold adjustment by detecting various living body information which shows the degree of the sympathetic tone and also, it is possible to carry out a delicate vagus nerve stimulation in response to the patient condition by adjusting the heart rate threshold and by controlling the nerve stimulation parameter at the same time.

It should be noted in the respective exemplified embodiments mentioned above that the heart rate measuring means was explained for measuring a heart rate, but it is also possible to replace it by a heartbeat interval. More specifically, the heart rate means a number of heartbeats per one minute and it is possible to calculate the heart rate by an interval between two consecutive heartbeats. Concretely speaking, assuming that a heart rate (times/min) is A and a heartbeat interval (second) is B, both thereof has the following relation:

$$A = 60/B \quad \text{(formula 1)}$$

It should be noted for B that not only the interval between two consecutive heartbeats but also an average value of the interval of three or more heartbeats can be used. As shown in the formula 1, a heart rate A and a heartbeat interval B are inversely proportional each other, so that the heart rate threshold in the exemplified embodiments is to be treated as the upper limit in case of a heart rate and as the lower limit in case of a heartbeat interval.

As mentioned above, according to the present invention, the degree of the patient sympathetic tone caused by a physical exercise or a stress is recognized by various living body information and it is possible to carry out the vagus nerve stimulation properly and delicately in response to the degree, so that enormous effects such as avoidance of side-effects caused by the nerve stimulation, avoidance of excessive lowering of the heart rate, power consumption saving or the like can be obtained.

The invention claimed is:

1. Heart treatment equipment comprising:
    nerve stimulation means for generating a nerve stimulation signal which stimulates a vagus nerve;
    heart activity measuring means for measuring a heart activity;
    heart activity threshold control means for setting a heart activity threshold when stimulating said vagus nerve by said nerve stimulation means;
    heart activity comparing means for comparing an output of said heart activity measuring means and said threshold; and
    sensor means for obtaining information indicating a physical exercise or a mental stress of a patient,
    wherein said heart activity threshold control means controls said threshold to decrease said threshold when the information obtained by the sensor means indicates an intense physical exercise or a mental stress of the patient.

2. Heart treatment equipment according to claim 1, wherein said heart activity measuring means measures a heart rate, and said nerve stimulation means generates said nerve stimulation signal in a case when said heart rate measured by said heart activity measuring means exceeds said threshold.

3. Heart treatment equipment according to claim 1, wherein said heart activity measuring means measures a heartbeat interval, and said nerve stimulation means generates said nerve stimulation signal in a case when said measured heartbeat interval goes under said threshold.

4. Heart treatment equipment according to claim 1 further comprising nerve stimulation signal control means for controlling a parameter of said nerve stimulation signal in response to the output of said sensor means.

5. Heart treatment equipment according to claim 4, wherein the parameter of said nerve stimulation signal is at least one of a period between pulses, a pulse width, a number of pulses, a pulse voltage, a pulse current, a delay time, a rest time and a repetitive number or a multiple combination chosen from these.

6. Heart treatment equipment according to claim 1, wherein said sensor means senses a vetricle contractility.

7. Heart treatment equipment according to claim 1, wherein said ventricle contractility is related to any one of a QT time, an intraventricular electrogram area, a pre-ejection time, a stroke volume and a ventricle pressure.

8. Heart treatment equipment according to claim 1, wherein said sensor means senses a body motion.

9. Heart treatment equipment according to claim 1, wherein said sensor means senses breathing.

10. Heart treatment equipment according to claim 1, wherein said sensor means senses blood.

11. A heart treatment method comprising:
    sensing a information indicating physical exercise or a mental stress of a patient;
    measuring a heart activity of the patient;
    comparing said measured heart activity with a threshold;
    stimulating a vagus nerve when it is judged by the comparison of the measured heart activity with the threshold that said heart activity increases; and
    decreasing said threshold when an intense physical exercise or a mental stress of the patient is sensed.

12. A heart treatment method according to claim 11, wherein a heart rate is measured as said heart activity and a nerve stimulation signal is generated in a case when said measured heart rate exceeds said threshold.

13. A heart treatment method according to claim 11, wherein a heartbeat interval is measured as said heart activity and a nerve stimulation signal is generated in a case when said measured heartbeat interval goes under said threshold.

14. A heart treatment method according to claim 11, wherein said information that is sensed is information relating to a ventricle contractility.

15. A heart treatment method according to claim 14, wherein said ventricle contractility is related to any one of a QT time, an intraventricular electrogram area, a pre-ejection time, a stroke volume and a ventricle pressure.

16. A heart treatment method according to claim 11, wherein said information that is sensed is information relating to a body motion of the patient.

17. A heart treatment method according to claim 11, wherein said information that is sensed is information relating to breathing of the patient.

18. A heart treatment method according to claim 11, wherein said information that is sensed is information relating to blood of the patient.

19. A heart treatment method according to claim 11, wherein a parameter of said nerve stimulation signal is further controlled in response to said sensed information.

20. A heart treatment method according to claim 19, wherein the parameter of said nerve stimulation signal is at least one of a period between pulses, a pulse width, a number of pulses, a pulse voltage, a pulse current, a delay time, a rest time and a repetitive number or a multiple combination chosen from these.

21. Heart treatment equipment comprising:
    nerve stimulation means for generating a nerve stimulation signal which stimulates a vagus nerve;
    heart rate interval measuring means for measuring a heart activity;
    heart rate interval threshold control means for setting a heart rate interval threshold when stimulating said vagus nerve by said nerve stimulation means;
    heart activity comparing means for comparing an output of said heart rate interval rate measuring means and said heart rate interval threshold; and
    sensor means for obtaining information indicating a physical exercise or a mental stress of a patient,
    wherein said heart rate interval threshold control means controls said heart rate interval threshold to increase said heart rate interval when the information obtained by the sensor means indicates an intense physical exercise or a mental stress.

22. Heart treatment equipment according to claim 21, wherein said nerve stimulation means generates said nerve stimulation signal when said measured heart rate interval falls below said heart rate interval threshold.

23. Heart treatment equipment according to claim 21, further comprising nerve stimulation signal control means for controlling a parameter of said nerve stimulation signal in response to the output of said sensor means.

24. Heart treatment equipment according to claim 23, wherein the parameter of said nerve stimulation signal is at least one of a period between pulses, a pulse width, a number of pulses, a pulse voltage, a pulse current, a delay time, a rest time and a repetitive number or a multiple combination chosen from these.

25. Heart treatment equipment according to claim 21, wherein said sensor means senses a vetricle contractility.

26. Heart treatment equipment according to claim 21, wherein said ventricle contractility is related to any one of a QT time, an intraventricular electrogram area, a pre-ejection time, a stroke volume and a ventricle pressure.

27. Heart treatment equipment according to claim 21, wherein said sensor means senses a body motion.

28. Heart treatment equipment according to claim 21, wherein said sensor means senses breathing.

29. Heart treatment equipment according to claim 21, wherein said sensor means senses a parameter pertaining to blood.

30. A heart treatment method comprising:

sensing physical exercise or a mental stress of a patient;

measuring a heart rate interval of the patient;

comparing said measured heart rate interval with a heart rate interval threshold;

stimulating a vagus nerve when it is judged by the comparison of the measured heart rate interval with the heart rate interval threshold that said heart activity increases; and increasing said heart rate interval threshold when an intense physical exercise or a mental stress of the patient is sensed.

31. A heart treatment method according to claim 30, further comprising generating a nerve stimulation signal when the measured heart rate interval falls under said threshold.

32. A heart treatment method according to claim 30, wherein a parameter of said nerve stimulation signal is further controlled in response to said sensed information.

33. A heart treatment method according to claim 32, wherein the parameter of said nerve stimulation signal is at least one of a period between pulses, a pulse width, a number of pulses, a pulse voltage, a pulse current, a delay time, a rest time and a repetitive number or a multiple combination chosen from these.

* * * * *